United States Patent [19]

Schmitt

[11] 4,346,709
[45] Aug. 31, 1982

[54] DRUG DELIVERY DEVICES COMPRISING ERODIBLE POLYMER AND EROSION RATE MODIFIER

[75] Inventor: Edward E. Schmitt, Palo Alto, Calif.

[73] Assignee: ALZA Corporation, Palo Alto, Calif.

[21] Appl. No.: 205,636

[22] Filed: Nov. 10, 1980

[51] Int. Cl.³ ............................................... A61M 7/00
[52] U.S. Cl. ....................................... 128/260; 424/19
[58] Field of Search ................... 128/260, 268; 424/16, 424/19

[56] References Cited

U.S. PATENT DOCUMENTS

| | | | |
|---|---|---|---|
| 3,867,519 | 2/1975 | Michaels | 128/260 |
| 4,066,747 | 1/1978 | Capozza | 128/260 |
| 4,070,347 | 1/1978 | Schmitt | 128/260 |
| 4,093,709 | 6/1978 | Choi et al. | 128/260 |
| 4,131,648 | 12/1978 | Choi et al. | 128/260 |
| 4,138,344 | 2/1979 | Choi et al. | 128/260 |

*Primary Examiner*—C. Fred Rosenbaum
*Attorney, Agent, or Firm*—Paul L. Sabatine; Edward L. Mandell

[57] ABSTRACT

Erodible devices are disclosed for delivering a drug to an environment of use. The devices comprise a body sized and adapted for delivering the drug to the environment of use, which body comprises (1) a poly(orthoester) or a poly(orthocarbonate) having a repeating unit consisting of a hydrocarbon radical and a symmetrical dioxycarbon unit of the general formula:

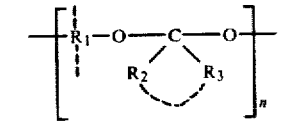

wherein $R_1$ is a multivalent hydrocarbon radical, $R_2$ and $R_3$ are hydrocarbon radicals with at least one of the $R_2$ or $R_3$ bonded to the dioxycarbon through an oxygen covalent bond, (2) a beneficial drug, and (3) an erosion rate modifier. The devices are useful for delivering both locally and systemically acting drugs over a prolonged period of time. A composition of matter is also disclosed comprising the poly(orthoesters) or the poly(orthocarbonates) and an erosion rate modifier.

100 Claims, 9 Drawing Figures

DRUG DELIVERY DEVICES COMPRISING ERODIBLE POLYMER AND EROSION RATE MODIFIER

FIELD OF THE INVENTION

This invention pertains to drug delivery devices. The devices comprise an erodible polymer, a drug, and an erosion rate modifier.

BACKGROUND OF THE INVENTION

Medical science has long recognized the value of drug delivery devices comprising a drug and an erodible polymer. These devices are valuable because the erodible polymer blended with an effective amount of a beneficial drug, erodes at a rate controlled by the inherent chemistry of the polymer itself. Therefore, the device, delivers the drug at a controlled rate and in an effective amount, to a biological environment of use. A major advance towards satisfying this recognition was met by the novel poly(orthoesters) and poly (orthocarbonates) disclosed in U.S. Pat. No. 4,180,646 issued to patentees Nam S. Choi and Jorge Heller. The patent discloses a unique class of polymers comprising a polymeric backbone having a repeating monomeric unit consisting of a hydrocarbon radical and a symmetrical dioxycarbon unit with a multiplicity of organic groups bonded thereto. These polymers reproducably erode in an aqueous or a biological fluid environment to innocuous products. The polymers are useful for delivering a beneficial agent at a controlled rate to the environment of use.

While the above polymers are outstanding and represent a pioneer advancement in the polymer and the drug delivery arts, and while they are useful for delivering numerous beneficial drugs to the environment of use, there is an occasional instance when it is desirable to modify the rate of erosion of the polymer to produce a more preferred dose rate of drug. For example, when the polymers are used in the form of implants in an animal environment of use, it may be therapeutically desirable to modify the rate of erosion of the polymer to achieve any one of a number of dose rates. The dose rates are adjusted by regulating the amount of drug released per unit time by the implant, which is controlled by the rate of polymer erosion. Controlling the release rate is also useful for extending the period of time the implant remains in the environment. It will be appreciated by those versed in the present arts, and in view of this presentation, that if an erosion rate modifier were made available for modifying the rate of erosion of the poly(orthoesters) and the poly(orhthocarbonates), such a modifier would represent a valuable contribution and a useful improvement in the polymer and delivering arts.

OBJECTS OF THE INVENTION

Accordingly, it is an immediate object of this invention to provide both novel and useful drug delivery device manufactured from erodible poly(orthoesters-orthocarbonates) and erosion rate modifiers for increasing the value and usefulness of the devices in the practicing arts.

Another object of the invention is to provide erosion rate modifiers for poly(orthoesters-orthocarbonates) that aid in regulating the rate of erosion of the polymers over time.

Yet another object of the invention is to provide devices for delivering drugs which devices contain erosion rate modifiers that change the period of time the devices erode and deliver the drugs.

Another object of the invention is to provide drug delivery devices comprising erosion rate modifiers that effect the amount of drug released as the devices erode over time.

Yet another object of the invention is to provide erodible devices having erosion rate modifiers therein, which alter the rate of erosion in aqueous and biological fluids over time.

Still another object of the invention is to provide drug delivery devices, possessing extended duration of therapeutic effects that leads to improved therapeutic outcome, and which devices are easy to manufacture with commercially available pharmaceutical manufacturing equipment.

Yet still another object of the invention is to provide bioerodible drug delivery devices embracing a structure formed of a non-toxic bioerodile orthoester polymer, or a non-toxic bioerodible orthocarbonate polymer, a non-toxic erosion rate modifier, and a drug.

Still another object of the invention is to provide a composition of matter comprising a poly(orthoester) or a poly(orthocarbonate) and an erosion rate modifier.

Other objects, features and advantages of the present invention will become more apparent from the following detailed description of the invention, and the appended claims defining the broad scope of the invention.

SUMMARY OF THE INVENTION

This invention concerns erodible delivery devices. The devices comprise a body formed of a polymeric backbone having a repeating monomeric unit of a hydrocarbon radical and a symmetrical dioxycarbon group with a multiplicity of organic groups bonded thereto. The polymers have a controlled degree of hydrophobicity which correspondingly controls the degree of erosion in aqueous and biological fluids. The devices additionally contain an erosion rate modifier that cooperates with the polymer for regulating the rate of erosion of the polymer. A drug in the device is released at a controlled rate and in a therapeutically effective amount as the polymer bioerodes over time. The invention also concerns compositions comprising the polymers and the erosion rate modifiers.

BRIEF DESCRIPTION OF THE DRAWINGS

In the drawings, which are not drawn to scale, but are set forth to illustrate various embodiments of the invention, the figures are as follows.

In the drawings and the specification, like parts in related figures are identified by like numbers. The terms appearing earlier in the specification, and in the description of the drawings, as well as embodiments thereof, are further described elsewhere in the disclosure.

DETAILED DESCRIPTION OF THE DRAWINGS

Figure 1:
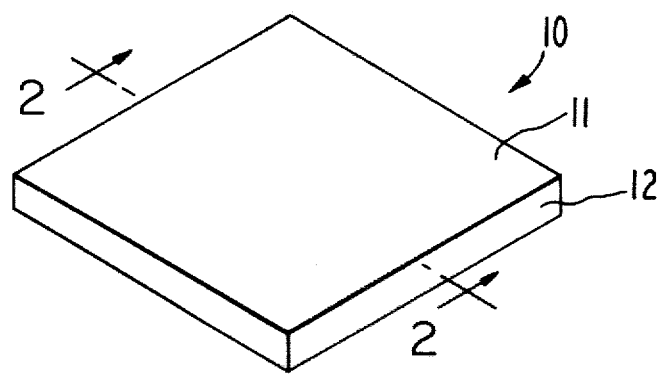
FIG. 1 is a view of a matrix made from the bioerodible polymer containing drug and release rate erosion modifier.

Turning now to the drawings in detail, which are examples of various drug delivery devices provided by the invention, and which examples are not to be construed as limiting, one embodiment of a delivery device is indicated in FIG. 1 by the numeral 10. In FIG. 1, device 10 comprises a matrix 12 made of a bioerodible poly(orthoester), or a bioerodible poly(orthocarbonate), which device 10 can be used for the continuous administration of an active drug, not seen in FIG. 1, to an organ, mucosa, derma or any drug receptor site. Device 10 delivers the drug by surface 11 bioeroding in a fluid environment at a controlled and continuous rate with the drug delivered at a corresponding controlled and continuous rate over a prolonged period of time.

Figure 2:
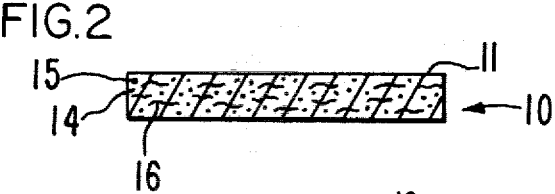
FIG. 2 is a cross-sectional view through 2—2 of FIG. 1 for illustrating the matrix having the drug and the modifier distributed throughout the matrix.

FIG. 2 is a cross-section through 2—2 of FIG. 1 for illustrating the internal structures of matrix 12 which defines device 10. Matrix 12 is formed of a drug release rate bioerodible poly(orthoester) or poly(orthocarbonate) 14, and it houses drug 15, represented by dots, and an erosion rate modifier 16, represented by wavy lines. Erosion rate modifier 16, used for the purpose of the invention, is a biologically acceptable material that cooperates with bioerodible polymer 14, for increasing the rate of erosion, or decreasing the rate of erosion of the polymer over time. A discussion of erosion rate modifiers is presented later in the specification.

Figure 3:
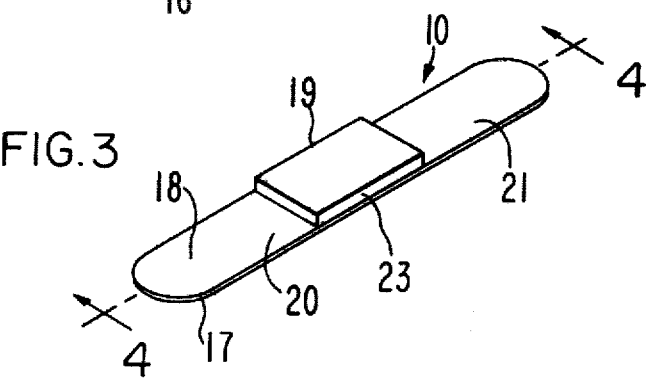
FIG. 3 is a perspective view of a drug releasing assembly manufactured in the form of a strip as provided by the invention.

FIG. 3 illustrates another drug delivery device 10 provided by the invention. Device 10, as seen in FIG. 3, is manufactured in the form of a strip 17. Strip 17 can be applied to the animal body by adhesive or mechanical means, and it comprises a main strip 18 formed of a flexible plastic such as polyurethane, polyvinyl chloride, natural rubber or aluminum foil having a central portion 19 with a pair of opposite side panels 20 and 21. The central portion has a raised section that forms a chamber 23 for housing a bioerodible polymer, which may include a fabric such as gauze or the like, or a thickening agent such as Cab-o-sil, not shown in FIG. 3. Side panels 20 and 21 serve as an attachment means for fixing strip 17 to a drug receptor surface, such as skin.

Figure 4:
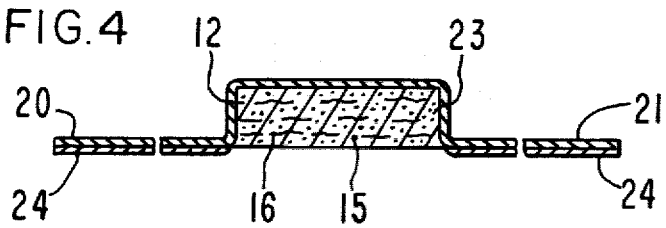
FIG. 4 is a side, sectional view of the internal structure of the drug releasing assembly manufactured in the form of a strip as shown in FIG. 3; and, FIG. 5 is a side view of a rod-like surgical implant provided by the invention for releasing drug in animal tissues.

FIG. 4 illustrates the structure of strip 17 taken through 4—4 of FIG. 3. In FIG. 4, a combination of the foregoing is shown, with chamber 23 operating as a medicament supplying depot. Chamber 23 comprises bioerodible polymer 14, represented by sectional lines, which polymer houses drug 15 and erosion rate modifier 16. Polymer 14 with or without gauze or thickening agents may possess adhesive-like properties for holding chamber 23 in tight contact with the skin, or optionally panels 20 and 21 can carry a thin layer of adhesive 24, such as silicone medical adhesive, a skin adhesive prepared by emulsion polymerization of dimethylaminoethyl methacrylate with an alkyl acrylate, or the like for tightly holding strip 17 on the skin.

Figure 5:
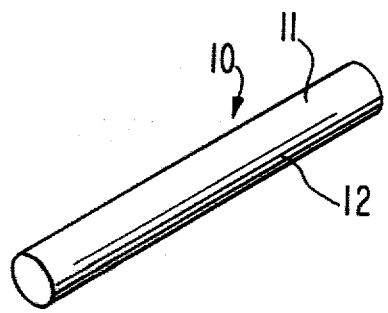

FIG. 5 depicts a side view of a rod-shaped drug delivery device 10 particularly adapted for use as an implant. Implant 10 is manufactured for administering a drug within an animal body at a controlled and continuous rate over a prolonged period of time. The depot implant is made from the bioerodible poly(orthoesters-orthocarbonates) discussed herein, and it houses drug and an erosion rate modifier, as previously described in FIG. 4. The implant can be introduced into the animal by a surgical operation, or the implant can be made as an injectable implant for easy insertion by trochar injection and prolonged retention in an animal drug receptor site such as a muscle. The implant is optionally sized, shaped and structured for placement subcutaneously, intradermally, or in a muscle of an animal wherein it bioerodes and releases drug over a prolonged period of time. Because the implant is bioerodible it requires only introduction into the animal, and because it erodes into innocuous products that are eliminated by the animal, and it never needs to be retrieved when all the drug is depolyed.

While FIGS. 1 through 5 are illustrative of various drug delivery devices that can be made according to the invention, it is to be understood these devices are not to be considered as limiting, as the devices can take a wide variety of shapes, sizes and forms that are structured and adapted for delivering drugs to the biological environment of use. For example, the devices include ocular, vaginal, buccal, nasal, anal-rectal, cervical, intrauterine, artifical gland, arterial, venous, ear, subcutaneous, topical, and intramuscular and like devices.

The drug delivery devices also can be manufactured as a spreadable composition useful for the controlled and continuous release of drug when applied to the environment of use by inunction. Additionally, the drug delivery device can be manufactured as pharmaceutical topical aerosols useful for applying spray-on preparations. The devices of the invention can be used in hospitals, clinics, nursing homes, veterinary clinics, the homes of individuals, and other like environments.

DETAILED DESCRIPTION OF THE INVENTION

In accordance with the practice of this invention, it has now been found that devices can be provided for delivering drugs for pharmaceutically acceptable therapy. The devices provide for the efficient administration of medicament at the site of application, they are compatible with animal tissues as they do not adversely affect their host, they are nonirritating and nontoxic, and their end-products, in the amount at which they are produced, are physiologically inactive. Additionally, the devices comprise a minimum number of components, they are easy to manufacture, and they can be manufactured in numbers at low cost.

The devices of the invention are made from drug release rate controlling bioerodible poly(orthoesters) and poly(orthocarbonates), erosion rate modifiers and drugs, wherein the polymers are represented by the following formula:

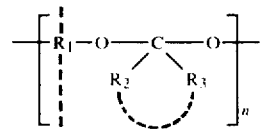

wherein (I) $R_1$ is a member selected from the group of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, and alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, and alkoxy of 1 to 7 carbons, alkenyl of 2 to 7 carbons, and an alkylene of 1 to 10 carbons; arylene of 6 to 12 carbons; arylene of 6 to 12 carbons substituted with an alkyl of 1 to 7 carbons, alkyloxy of 1 to 7 carbons, an alkenyl of 2 to 7 carbons, and an alkylene of 1 to 10 carbons; wherein (II) $R_2$ and $R_3$ are alkyl of 1 to 7 carbons, alkenyl of 2 to 7 carbons, aryl of 6 to 12 carbons, an oxygen atom covalently bonded to the dioxycarbon atom, and when an oxygen atom $R_2$ and $R_3$ are a member independently selected from the group consisting of alkyloxy of 1 to 7 carbons; alkenyloxy of 2 to 7 carbons; and aryloxy of 6 to 12 carbons; and when only one of $R_2$ and $R_3$ is selected from said member the other $R_2$ and $R_3$ is selected from the group consisting of alkyl of 1 to 7 carbons; alkenyl of 2 to 7 carbons; and aryl of 6 to 12 carbons; wherein (III) $R_2$ and $R_3$ are intramolecularly covalently bonded to each other and to the same dioxycarbon atom, with at least one of $R_2$ and $R_3$ a ring oxygen atom, forming a heterocyclic ring of 5 to 8 carbon and oxygen atoms when $R_2$ and $R_3$ are selected from the group consisting of alkylene of 2 to 6 carbons; alkenylene of 2 to 6 carbons; alkylenoxy of 2 to 6 carbons; alkenyleneoxy of 2 to 6 carbons; alkylenedioxy of 2 to 5 carbons; alkenylenedioxy of 2 to 5 carbons; oxa; and a heterocyclic ring of 5 to 8 carbon and oxygen atoms substituted with an alkyl of 1 to 7 carbons, an alkyloxy of 1 to 7 carbons, an alkenyl of 2 to 7 carbons, and an alkenyloxy of 2 to 7 carbons; wherein (IV) $R_2$ and $R_3$ are intramolecularly covalently bonded to each other and to the same dioxycarbon atom, with a least one of $R_2$ and $R_3$ is a ring oxygen atom forming a fused polycyclic ring of 8 to 12 carbon and oxygen atoms when $R_2$ and $R_3$ are a member selected from the group consisting an aralkylene of 8 to 12 carbons; aralkenylene of 8 to 12 carbons; aryloxy of 8 to 12 carbons; aralkyleneoxy of 8 to 12 carbons; aralkenyleneoxy of 8 to 12 carbons; aralkylenedioxy of 8 to 12 carbons; aralkenylenedioxy of 8 to 12 carbons; oxa; and a fused polycyclic ring of 8 to 12 carbon and oxygen atoms substituted with an alkyl of 1 to 7 carbons, an alkyloxy of 1 to 7 carbons; an alkenyl of 2 to 7 carbons; and an alkenyloxy of 2 to 7 carbons; wherein (V) $R_2$ and $R_3$ are intramolecularly covalently bonded to each other and to the same dioxycarbon atom to form a 5 to 6 member carbocyclic ring; and n is 10 to $10^7$.

The term alkylene as used in this specification and the accompanying claims denotes a straight or branched divalent, trivalent or tetravalent alkylene radical such as 1,2-ethylene; 1,3-propylene; 1,2-propylene; 1,4-butylene; 1,5-pentylene; 1,6-hexylene; 1,2,5-hexylene; 1,3,6-hexylene; 1,7-heptylene; 2-methyl-1,7-heptylene; 1,8-octylene; 1,10-decylene; and the like.

The term alkenylene denotes an unsaturated, straight or branched chain such as 1,4-but-2-enylene; 1,6-hex-3-enylene; 1,7-hept-3-enylene; 1,8-oct-3-enylene; 1,9-non-3-enylene; 4-propyl-(1,6-hex-3-enylene); 5-methoxy-(1,6-hex-3-enylene); 2-propenyl-(1,6-hex-3-enylene); and the like.

The term cycloalkylene includes monocyclic cycloalkylene radicals such as cyclopropylene; cyclobutylene; cyclopentylene; cyclophexylene; and cycloheptylene. Similarly, the phrase cycloalkylene substituted with an alkyl, and alkyloxy, an alkenyl, or alkylene includes substituted cycloalkylenes such as 2-methyl-1,3-cyclopropylene; 2-methyl-1,4-cyclopentylene; 2-methyl-1,6-cyclohexylene; 1-methylene-cyclohexylene; 1,6-dimethylene-cyclohexylene; 2-ethoxy-2,3-cyclopropylene; 5-butoxy-1,4-cyclopentylene; 2-methoxy-1,4-cyclohexylene; 2-propenyl-1,5-cyclopentylene; 2-isobutenyl-1,6-cyclohexylene; and the like.

Exemplary cycloalkenylene and cycloalkenylene substituted with an alkyl, an alkoxy, an alkenyl, or an alkylene include monocyclic cycloalkenylenes such as 1,4-cyclopent-2-enylene; 1,5-cyclopent-3-enylene; 1,6-cyclohex-2-enylene; 1,6-dimethylene-cycohex-2-enylene; 5-methyl-(1,4-cyclo-pent-2-enylene); 6-ethyl-(1,4-cyclohex-2-enylene); 6-ethoxy-(1,5-cyclohex-2-enylene); 2-propyl-(1,5-cyclohex-3-enylene); 2-methoxy-(1,4-cyclohex-2-enylene); 2-methoxy-(1,4-cyclohept-2-enylene); 1-methylene-(1,6-cyclohex-2-enylene); and the like.

The expressions arylene and arylene substituted with an alkyl, an alkenyl, an alkoxy or an alkylene include the benzoid groups such as phenylene; phenylalkylene; phenylalkenylene; 1,4-phenyl-dimethylene; 1,4-phenyl-diethylene; 2-ethyl-1,4-phenyldimethylene; 2-methyl-1,4-phenyl-dimethylene; 2-methoxy-1,4-phenylene; 2-propyl-1,4-phenylene; 2-propylene-1,4-phenyldimethylene; naphthalene; and the like.

The term alkyl embraces straight and branched chain alkyl radicals such as methyl; ethyl; n-propyl; n-butyl; n-amyl; n-hexyl; n-heptyl; and the various positional isomers such as isopropyl; t-butyl; sec-butyl; isoamyl; isohexyl; t-heptyl; and the like.

The term alkenyl embraces straight and branched chain lower alkenyl groups such as 1-propenyl; 2-propenyl or allyl; 1-butenyl; 2-butenyl; 1-pentenyl; 2-ethenyl; and the corresponding positional isomers such as 1-isobutenyl; 2-isobutenyl; 2-sec-butenyl; 2-methyl-1-butenyl; 2-methyl-2-pentenyl; 2,3-dimethyl-3-hexenyl; and the like.

The terms alkoxy or alkyloxy include the straight and branched chain lower groups, and the positional isomers thereof, such as methoxy; ethoxy; propoxy; butoxy; n-pentoxy; n-hexoxy; isopropoxy; 2-butoxy; isobutoxy; 3-pentoxy; and the like.

The term alkenyloxy embraces straight and branched chain lower alkenyloxy groups and the positional isomers thereof, such as ethenoxy; propenoxy; butenoxy; pentenoxy; hexenoxy; isopropenoxy; isobutenoxy; sec-butenoxy; 2-methyl-1-butenoxy; 2-methyl-2-butenoxy; 2,3-dimethyl-3-butenoxy; and the like.

The term alkyleneoxy comprehends straight and branched chain alkyleneoxy radicals such as 1,3-propyleneoxy; 1,4-butyleneoxy; 1,5-pentyleneoxy; 1,6-hexyleneoxy; 2,2-dimethyl-1,4-butyleneoxy; and the like. Similarly, the term alkenyleneoxy comprehends radicals such as prop-1-enyleneoxy; 1,4-but-1-enyleneoxy; 1,4-but-2-enyleneoxy; 1,5-pent-1-enyleneoxy; 1,6-hex-1-enyleneoxy; and the like.

The expressions alkylenedioxy and alkenylenedioxy include straight and branched chain radicals such as 1,3-propylenedioxy; 1,4-butylenedioxy; 1,5-pentylenedioxy; 1,6-hexylenedioxy; and 1,7-heptylenedioxy; 1,3-prop-1-enylenedioxy; 1,4-but-1-enylenedioxy; 1,4-but-2-enylenedioxy; 1,5-pent-1-enylenedioxy; 1,6-hex-1-enylenedioxy; and the like.

The terms aryloxy, aralkyleneoxy, aralkenyleneoxy; aralkylenedioxy; and aralkenylenedioxy indicate an aryl such as phenyl, aryloxy a phenyloxy, with the alkyleneoxy, alkenyleoneoxy, alkylenedixoy and alkenylenedioxy area as defined above.

The phrase, heterocyclic ring of 5 to 8 carbon and oxygen atoms formed when $R_2$ and $R_3$ are taken together, are represented by heterocyclic rings such as dioxolanyl; dioxanyl; dioxepanyl; dioxocanyl; dioxonanyl; tetrahydrofuranyl; furyl; dihydrofuranyl; pyranyl; ocanyl; and oxepanyl.

The phrase, fused polycyclic ring with at least one or two ring forming oxygen atoms define a ring structure in which a heterocyclic and an aryl ring have two carbon atoms in common, are for example, a member selected from the group consisting of benzfuryl; benzpyranyl; 4,5-benz-1,3-dioxepanyl; 5,6-benz-1,3,-dioxepanyl; 4,5-benz-1,3-dioxolanyl; 4,5-benz-1,3-dioxyolanyl; 4,5-benz-1,3-dioxocanyl; 5,6-benz-1,3-dioxocanyl; 6,7-benz-1,3-dioxocanyl; 6,7-benz-1,3-dioxocanyl; and benz-1,3-dioxanyl.

The phrase carbocyclic ring of 5 to 6 carbons formed when $R_2$ and $R_3$ are taken together are represented by rings such as cyclopentylene; cyclohexylene; cyclopentenylene; cyclopentadienylene; and phenylene.

The poly(orthoesters), and the poly(orthocarbonates) described herein are known to the prior art in U.S. Pat. Nos. 4,093,709; 4,131,648; 4,138,344; and 4,180,646. These patents are issued to patentees Nam S. Choi and Jorge Heller, and they are assigned to the ALZA Corporation of Palo Alto, Calif., the assignee of this application.

The phrase, erosion rate modifier as used herein, denotes a material that assists in controlling the rate of erosion of the erodible poly(orthoesters), or the rate of erosion of the poly(orthocarbonates) used for the purpose of the invention. The modifiers can decrease the rate of erosion of the polymers and correspondingly increase the period of time the drug delivery device is in the environment of use releasing drug, or the modifier can increase the rate of erosion and correspondingly decrease the period of time the drug delivery device is in the environment of use releasing drug.

The erosion rate modifiers that increase or prolong the life of devices made from the erodible polymers are materials that mix with the polymers and drugs, and when the device is in a fluid environment of use, the modifier aids in producing an environment exhibiting a pH of at least 7 or greater at the polymer-modifier-fluid-drug interface. The erosion rate modifiers that decrease or lessen the life of devices made from the erodible polymers are materials that mix with the polymers and drugs, and when the device is in a fluid environment of use, the modifier aids in producing an environment exhibiting a pH of 7 or less at the polymer-modifier-fluid-drug interface.

Erosion rate modifiers that decrease the rate of erosion or prolong the life of the devices include a member selected from the group consisting of metal oxides such as binary compounds of oxygen; salts of electronegative nonmetal oxides such as mono, and dihydrogen phosphates, carbonates, sulfates, and the like; hydrides such as compounds of hydrogen with an electro-positive element such as lithium, sodium, potassium, magnesium, aluminum, alkali earths, and the like; metals, and hydroxides of alkali earth metals; and tertiary compounds of nitrogen such as amines, substituted amines and the polyamines. Erosion rate modifiers that increase the rate of erosion or shorten the life of the devices include a member selected from the group consisting essentially of organic acids, inorganic acids, Lewis acids, monobasic acid salts, polybasic acid salts, and hydroxides of nonmetals. The amount of modifier used for the present purpose generally is about 0.001% to 40% by weight based on 100% by weight of the device. Additionally, the device can contain a multiplicity of erosion rate modifiers as used for the intended purpose.

Representative salts of electronegative nonmetal oxides include mono and dihydrogen phosphates, carbonates, sulfates and the like. Representative hydrides include compounds of hydrogen with electro-positive elements such as lithium, sodium potassium, magnesium, aluminum, and alkali earth.

Representative metal oxides include aluminum oxide, calcium oxide, lithium oxide, magnesium oxide, potassium oxide, and sodium oxide.

Representative salts of nonmetal oxides include calcium carbonate, lithium carbonate, magnesium carbonate, sodium acid carbonate, potassium carbonate and sodium carbonate; calcium phosphate, lithium phosphate, disodium hydrogen phosphate, magnesium phosphate, magnesium phosphate, manganese phosphate, potassium dihydrogen phosphate, potassium phosphate, sodium hydrogen phosphate, sodium phosphate, calcium sulfite, lithium sulfite, magnesium sulfite, potassium sulfite and sodium sulfite; and lithium sulfate, potassium sulfate, sodium sulfate, and the like.

Representative metals include a member selected from the group consisting essentially of aluminum, calcium, lithium, sodium, magnesium, and potassium.

Representative hydride include a member selected from the group consisting of aluminum hydride, calcium hydride, lithium hydride, magnesium hydride, potassium hydride, and sodium hydride.

Representative hydroxides useful for the present purposes include compounds selected from the group consisting of aluminum hydroxide, barium hydroxide, calcium hydroxide, lithium hydroxide, magnesium hydroxide, potassium hydroxide, and sodium hydroxide.

Representative amine compounds include trimethylamine, triethylamine, tridecylamine, hydroxylamine, polylysine, propylamine, polypropylamine, ethylenediamine, and 2-hydroxy-1-aminopropane.

Representative organic and inorganic acids include amino acids, amygladic, adipic, boric, citric, fumaric, itaconic, lactic, glycine, malic, maleic, mesaconic, oxalic, phthalic, phosphoric, succinic, sulfamic, and tartaric. Lewis acids include aluminum chloride, stannic chloride, and mixtures thereof.

Representative of monobasic or polybasic acids, and acid salts include potassium tetraoxalate, potassium hydrogen tartrate, potassium hydrogen phthalate, sodium tetraoxalate, sodium hydrogen tartrate, sodium hydrogen phthalate, a mixture of sodium tetraoxalate and sodium acid carbonate, potassium dihydrogen citrate, sodium dihydrogen citrate, citric acid and sodium acetate, glycine and citric acid, and sodium p-toluenesulfonate, and p-toluenesulfonic acid.

The inorganic and organic compounds used for the novel purpose of the invention are disclosed in *Handbook of Chemistry and Physics*, 57th Edition, pags D-133 to D-134, 1976, published by CRC Press, Cleveland, Ohio; *Encyclopedia of Chemical Technology*, Vol. 11, pages 389 to 390, 1971, published by WileyInterscience, New York; *Lange's Handbook of Chemistry*, pages 5–73 to 5–80, 1979, published by McGraw-Hill, New York; and in the *The Chemist's Companion*, by Gordon et al., pages 71 to 72, published by Wiley Interscience, New York.

The term drug as used herein denotes both locally and systemically acting drugs. Generically, the drugs include a member selected from the group consisting of analgesic, anorexic, antiarthritic antibacterial, antibiotic, anticonvulsant, anti-depressant, antidiabetic, antifungal, antihistaminic, anti-hypertensive, antineoplastic, antiparkinsonism, antipyretic, anticholinergic, anti-inflammatory, anesthetic, antimicrobial, antiviral, anti-ulcer, bronchial dilator, cardiovascular, contraceptive, central nervous system, drugs that act on muscles and tissues, drugs that act in passageways and cavities, drugs that act on the circulatory system, decongestants, hypoglycemics, hormone, hypnotic, hematinic, electrolyte, germicide, muscle relaxant, parasympatholytic, parasympathomimetic, psychostimulant, ophthalmic, sedative, sympathomimetic, tranquilizer, uterine, vaginal, vitamin, vasodilator, vasopressor, and the like. The drugs and their dosage unit amounts for humans are well known in *Pharmacology in Medicine,* by Drill and edited by DiPalma, 1965, published by McGraw-Hill, New York; in *Pharmacological Basis of Therapeutics,* by Goodman and Gilman, 4th Edition, 1970, published by MacMillian Co., and in U.S. Pat. No. 3,977,404. The amount of drug present in a device provided by the invention will be about 0.5% to 50% by weight, with a more presently preferred amount of about 10% to 40% by weight.

Examples of presently preferred drug that are administered by the devices over a prolonged period of time are hormones selected from the group consisting of cortical, androgenic, estrogenic and progestational hormones. Representative cortical hormones include aldosterone, desoxycorticosterone, cortisone, hydrocortisone, prednisone, prednisolone, triamcinolone, paramethasone, dexamethasone; fludrocortisone acetate, flurandrenolone acetonide, betamethasone benzoate, dexamethasone phosphate, methyl prednisolone, prednisolone acetate, triamcinolone acetonide, and the like.

Representative of estrogenic hormones include a member selected from the group consisting essentially of estradiol, $\beta$-estradiol, 3-benzoate estradiol, 3-acetate estradiol, 17-$\beta$acetate estradiol, 17-$\beta$propionate estradiol, 17-$\beta$heptanoate estradiol, 17-undecanoate estradiol, 17-valerate estradiol, 3-methyl ether estradiol, 3,17-$\beta$diacetate estradiol, 3,17$\beta$-dipropionate estradiol, hemisuccinate estradiol, estradiol 17$\beta$-cypionate, 17$\beta$-estradiol disodium diphosphate, 17-$\beta$-estradiol disodium sulfate, 17$\beta$-estradiol-3(disodium phosphate), 17 $\beta$-estradiol-17(disodium phosphate), estriol, estrone, ethinyl estradiol, estrazinol, estrofurate, quinestrol, and the like, and mixtures thereof.

Representative of progestational hormones include natural progestins such as progesterone and preganediol, and synthetic progestins such as a member selected from the group consisting of algestone acetophenide, azacosterol hydrochloride, chlormadinone acetate, dyhydrogesterone, ethisterone, hydroxyprogesterone, medrogestone, medroxy-progesterone, megestrol acetate, melengestrol acetate, allylestrenol, ethynodiol diacetate, lynestrenol, norethindrone (also known as norethisterone), norethindrone acetate, norethynodrel, norgesterone, norgestrel, norgestrienone, norvinisterone, oxogestone, quingestrone, quingestanol acetate, and tigestol.

Representative androgens include testosterone, testosterone propionate, methyl testosterone, mesterolone, fluoxymesterone, methandriol, methandrostenolone, methenolone enanthate, nandrolone, norethandrolone, oxymetholone, stanozolol, zeranol, and the like.

Representative drugs useful for the management of diabetes that can be administered by the delivery devices of the invention include insulin, neutral insulin, zinc insulin, dalanated insulin, zinc globin insulin, isophane insulin, protamine insulin, extended zinc insulin, insulin derived from animal sources, insulin prepared from bacterial sources, sulfonylurea hypoglycemics, acetohexamide, glypinamide, chlorpropamide, tolazamide, tolbutamide, phenformin, and the like.

Representative of other drug species that can be delivered include penicillin, cephalosporins, erythromycin, lincomycin, tetracycline, streptomycins. bethanidine, clonidine, debrisoquin, amyl nitrite, glyceryl trinitrate, octyl nitrate, clonitrate, erythrityl tetranitrate, isosorbide dinitrate, mannitol hexanitrate, pentaerythritol tetranitrate, pentrinitrol, propatylnitrate, theophylline, dopa, methyldopa, epinephrine, norepinephrine, dopamine, mephenesin, indomethacin, alcolfenac, fenoprofen, fluprofen, ibufenac, ibuprofen, naproxen, kitoprofen, naproxol, fenbufen, meprobamate, chlorpromazine, timolol, metoprolol, aspirin, acebutolol, acetophenetidin, ascorbic acid, oxprenolol, and the like. The specific drugs disclosed herein, their dosage unit amount, and their pharmaceutical activity are disclosed in *Cutting's Handbook of Pharmacology,* 6th Ed., 1972, published by Appleton-Century-Crofts, New York, and in *Physicians' Desk Reference,* 34th Ed., 1980, published by Medical Economics Co., Oradell, N.J.

The devices of the invention can be manufactured by standard techniques. For example, the bioerodible polymers mixed with release rate modifiers and drugs can be extruded into filaments, spun into fibers, extruded, pressed into shaped articles, solvent film cast, doctor-bladed into thin films, coated by solvent evaporation, coated by using a fluidized bed, compression and transfer molded, and like methods of manufacture. In the process of manufacturing the devices, the materials and ingredients used are predried, and the mixing and fabrication procedures are carried out in an inert, dry atmosphere.

The devices made by these processes can be a single matrix, a container with a reservoir, or a number of layers. The devices can be manufactured into various shapes, for example, flat, square, round, tubular, disc, ring, and the like. Also, the devices can be manufactured, sized, shaped, structured and adapted for implantation, insertion, placement, retention, depositing or spreading on the body, in body cavities, and passageways of the body of animals, which latter term embraces warm-blooded animals, and humans. Standard procedures for processing the polymers, modifiers, and the drugs, are described in the *Plastic Encyclopedia,* Vol. 46, 1969, published by McGraw-Hill, Inc.

DETAILED DESCRIPTION OF EXAMPLE

The following examples are set forth as representative methods illustrative of the spirit of the present invention. These examples are not to be construed as limiting the scope of the invention, as these and other functionally equivalent methods will be readily apparent to those skilled in the subject art.

EXAMPLE 1

A bioerodible drug delivery device was prepared as follows: to 90 grams of dry poly(2,2-dioxo-cis/trans-1,4-cyclohexane dimethylene tetrahydrofuran) was added 10 grams of hydrocortisone and the polymer and drug thoroughly blended to form a homogenous composition. The hydrocortisone was previously dried under vacuum at 60 degrees C. for at least 8 hours. The hydrocortisone was thoroughly blended with the polymer to yield the composition by heating them to 130 degrees C. and mixing them in a blender. The blending was done in a vacuum drybox, and the polymer and drug were blended on a Teflon ® sheet heated on a hot plate.

Next, the homogenous composition was pressed into a 10 mil thick sheet using a Carver ® press in a Labconco ® drybox having a nitrogen atmosphere. The composition was pressed at 24,000 psi at 130 degrees C. between Teflon ®-aluminum sheets with the Teflon ® facing the polymer-drug composition. After pressing, the sheet was transferred to a vacuum drybox having a helium atmosphere, and a drug delivery device was die-cut with a 5 mm × 8 mm oval punch. This device served as a control for determining the amount of drug released over time. The release rate was determined by placing the device in a 30 ml aqueous bath, at 37 degrees C., having a pH of 7.1, obtained by using a 0.1 N phosphate buffer. The release of hydrocortisone was measured by U.V. absorption at 245 mμ.

EXAMPLE 2

Figure 6:
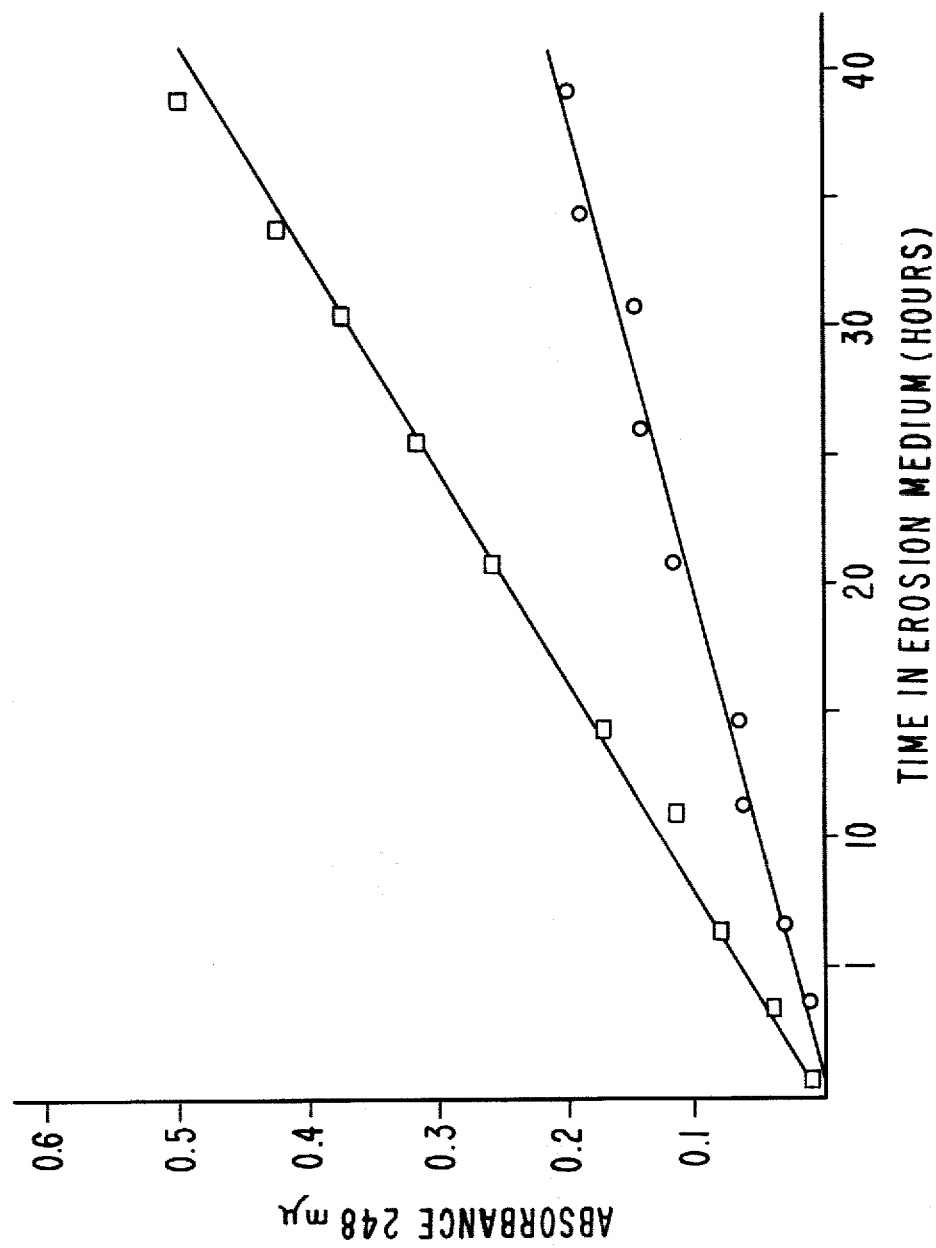
FIGS. 6 to 8 indicate results obtained by using the modifiers of the invention.
Figure 7:
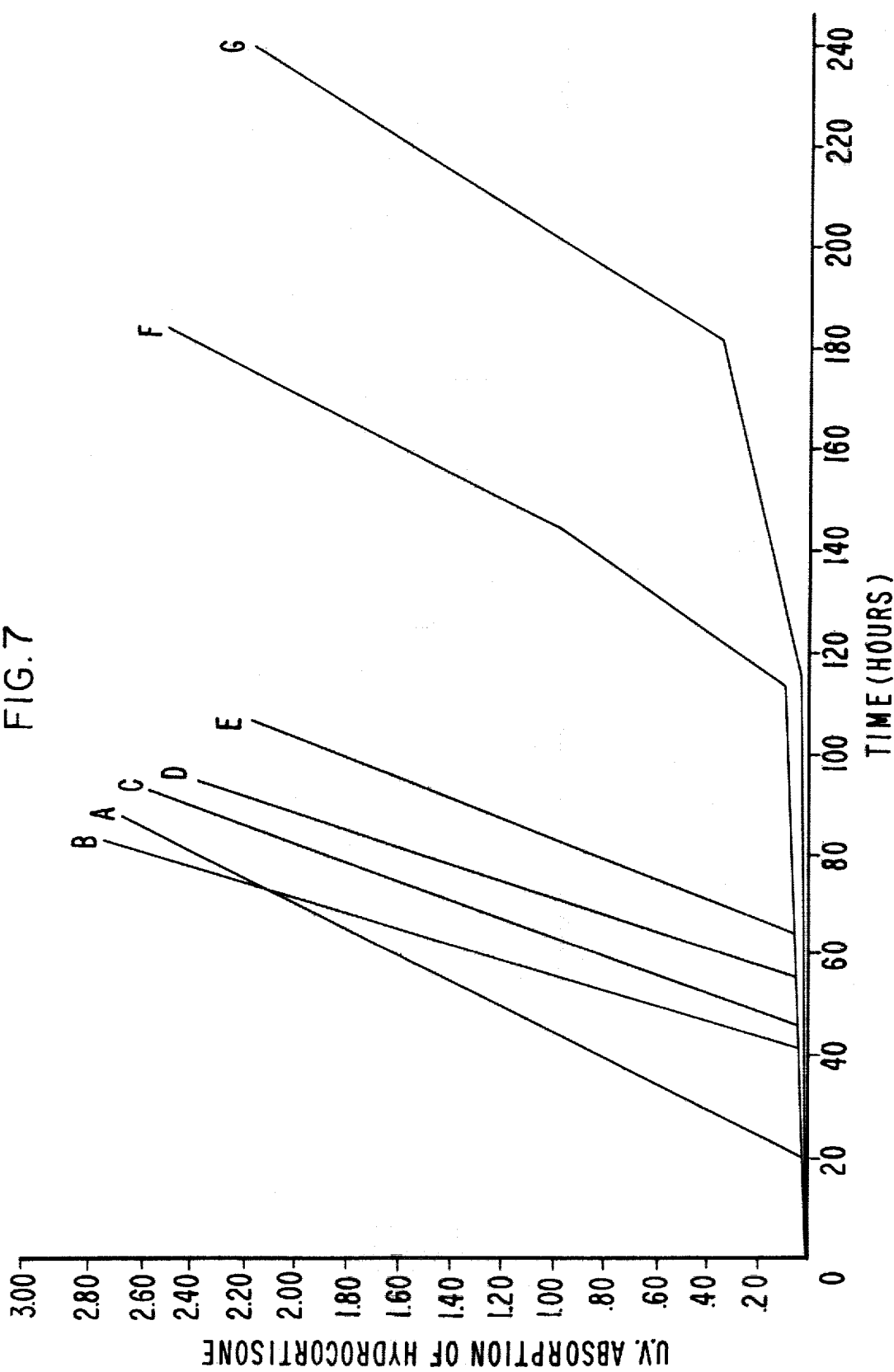

The procedure described in Example 1 was repeated and a drug delivery device was prepared, comprising the polymer, poly(2,2-dioxo-1,6-hexamethylene tetrahydrofuran), 5% by weight hydrocortisone, 12.4% by weight of CaO. A control system was prepared to demonstrate the release pattern of an identical device prepared without the rate controlling agent, CaO. The release of hydrocortisone into a 0.1 molar phosphate buffer having a pH of 7.4 maintained at 37° C. is indicated in FIG. 6. In FIG. 6, the line connecting the circular symbols show a relative release rate of hydrocortisone from the device containing 12.4% CaO which is approximately one-half of the release rate shown by the device made without any CaO (square symbols). The units along the abscissa indicate the absorbance of a specific wave length of ultraviolet light. An additional series of drug delivery devices were prepared containing the same polymer and drug of Example 1, and the erosion rate modifier, calcium oxide in the following weight percents: 0.1%, 0.3%, 1.0%, 3.0%, and 10%. The results for Example 1 and of the additional series of Example 2 are set forth in FIG. 7. In FIG. 7, A indicates the control of Example 1, B indicates a device containing 0.1%, CaO, C indicates a device containing 0.3% CaO, D indicates 1% CaO, E indicates another device containing 1% CaO, F indicates a device containing 3% CaO, and G indicates a device containing 10% CaO.

EXAMPLE 3

Figure 8:
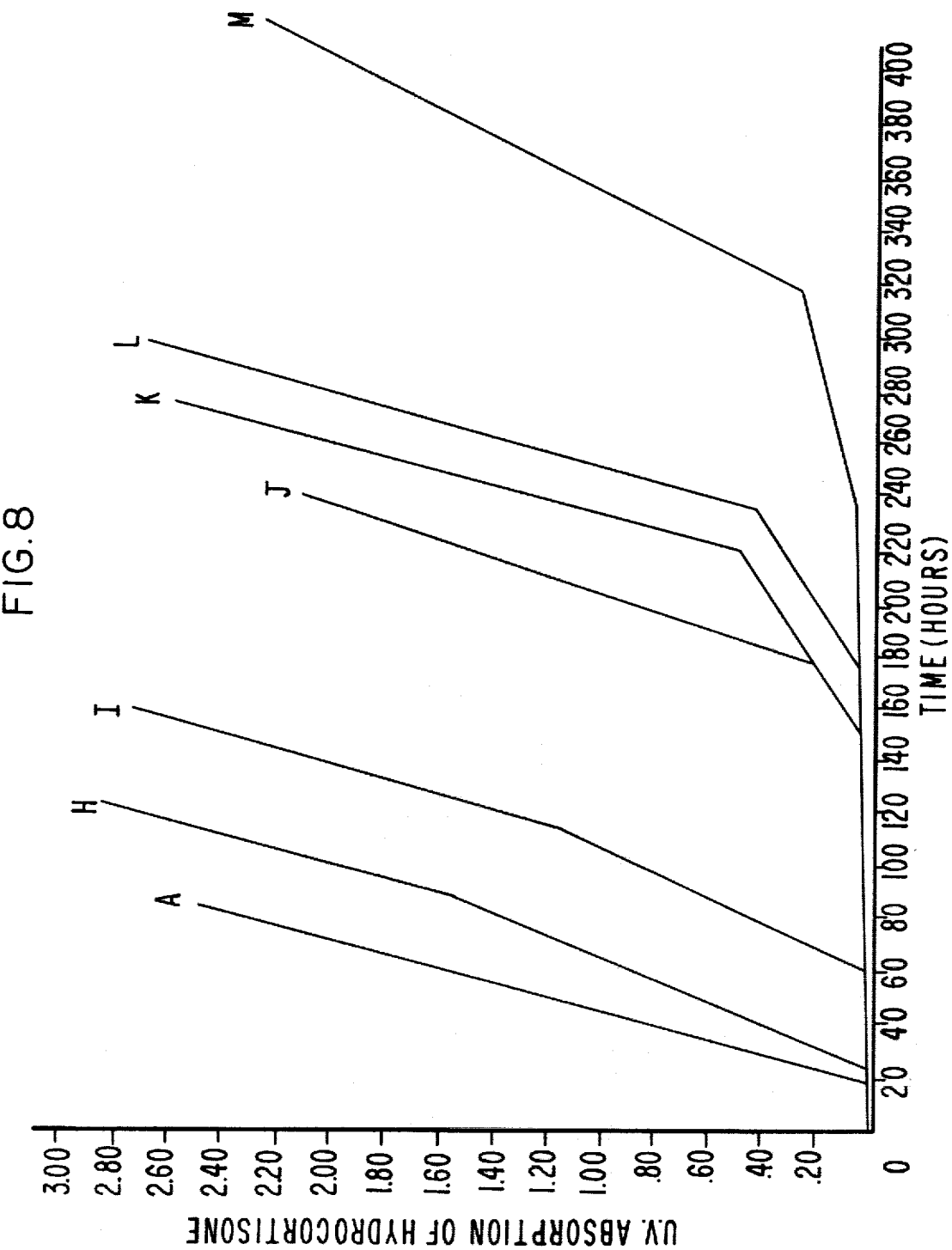

The procedure of Example 1 was followed in this example, with the erodible device made of the same polymer, containing 10% hydrocortisone, and a 10% of an erosion rate modifiers. A series of erosion rate modifiers were used to demonstrate the increased life of the devices. The results obtained for the modifiers are set forth in FIG. 8, wherein the modifiers are as follows: A indicates a control made without a modifier, H indicates a device containing the modifier calcium dibasic phosphate, I indicates a device containing calcium phosphate, J indicates a device containing calcium oxide, K indicates a device containing magnesium carbonate, L indicates the erosion rate of another device containing 10% magnesium carbonate, and M indicates the erosion rate of a device containing 10% sodium carbonate.

EXAMPLE 4

Figure 9:
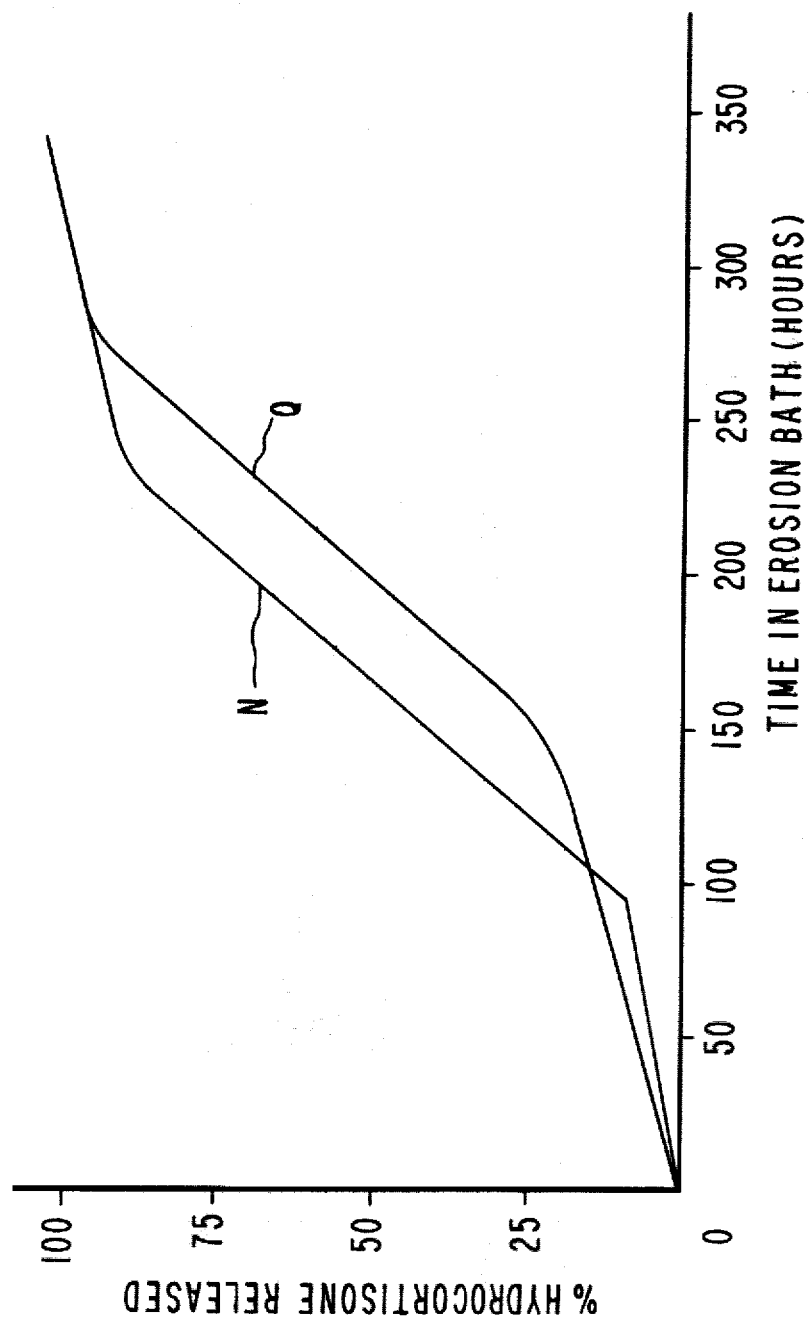

The procedure of Example 1 was followed in this example. In this example, an erodible device was prepared comprising 5% hydrocortisone, 10% calcium oxide and 85% poly(2,2-dioxo-cis/trans-1,4-cyclohexane dimethylene tetrahydrofuran), which device exhibits a release rate profile identified as N in FIG. 9; and a device comprising 5% hydrocortisone, 5% sodium carbonate, 5% sodium bicarbonate, and 85% poly(2,2-dioxo-cis/trans-1,4-cyclohexane dimethylene tetrahydrofuran), which device exhibits a release rate profile identified as Q in FIG. 8.

EXAMPLE 5

A bioerodible drug delivery device, manufactured as an implant, for releasing a contraceptively effective amount of a steroid over a prolonged period of time was manufactured using the anhydrous drying and process techniques described in Examples 1 through 4. The device of this example was manufactured as follows: first, 70 grams of a bioerodible polymer of the following structure was heated in a commercial blender to 120 degrees C. The polymer had a molecular weight of about 35,000, and the blender had a dry nitrogen atmosphere. Next, 20 grams of dry sodium carbonate was added to the polymer,

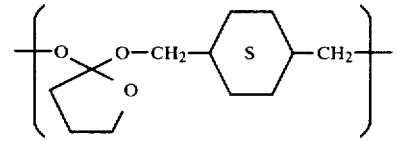

and the two ingredients blended for 5 minutes. The blender mixed the ingredients with an internal stirrer set at 200 revolutions per minute. Then, 10 grams of dry d-norethisterone was added to the blender and the three ingredients blended for 10 minutes to form a homogenous composition.

After blending, the composition was transferred to a mold having a series of cavities shaped as implants. The mold was in a dry box, under a helium atmosphere. The composition was charged into the mold, and pressed into implants under a pressure of 20,000 psi, at 110 degrees C. The implants were shaped as rods 14 mm long by 3 mm in diameter with rounded ends, and they weighed about 125 mg. The implants, when in operation in vivo, exhibit a rate of release of about 150 g per day of norethisterone over a prolonged period of about 4 months.

EXAMPLE 6

Three implants, designed for subcutaneous or intramuscular implantation were prepared in a blender, under anhydrous conditions, by separately blending predried ingredients such as, (a) 70 grams of poly(2,2-dioxo-cis/trans-1,4-cyclohexane dimethylene-2-tetrahydrofuran), 10 grams of micronized calcium oxide, and 20 grams of micronized norethindrone; (b) 70 grams of poly(2,2-dioxo-cis/trans-1,4-cyclohexane dimethylene-2-tetrahydrofuran), 5 grams of micronized calcium oxide, and 25 grams of micronized norethindrone; and (c) 75 grams of poly(2,2-dioxo-cis/trans-1,4-cyclohexane dimethylene-2-tetrahydrofuran), 5 grams of micronized calcium oxide, and 20 grams of micronized norethindrone. The time of blending was 20 minutes, at 110 degrees C., with a stirrer speed of 25 revolutions per minute, rpm. The three blends were injection molded into implants 14 mm×3 mm, with each weighing about 120 mg. The systems contained 24 to 32 mg of norethindrone, and released about 200 μg/day of the steroid.

EXAMPLE 7

The procedures set forth in the above examples were followed for making a series of implants comprising 50 to 80% of poly(2,2-dioxo-cis/trans-1,4-cyclohexane dimethylene-tetrahydrofuran), from 5 to 30% of the erosion rate modifier selected from the group consisting of sodium carbonate and magnesium oxide, and from 5 to 30% of the contraceptive steroid norethindrone. The implant had a presently preferred composition of (a) 70% of poly(2,2-dioxo-cis/trans-1,4-cyclohexane dimethylene-tetrahydrofuran), 10% of sodium carbonate and 20% of norethindrone; (b) 55% of poly(2,2-dioxo-cis/trans-1,4-cyclohexane dimethylene-tetrahydrofuran), 20% of sodium carbonate, and 25% of norethindrone; (c) 50% of poly(2,2-dioxo-cis/trans-1,4-cyclohexane dimethylene-tetrahydrofuran), 20% of sodium carbonate and 30% of norethindrone; (d) 90% of poly(2,2-dioxo-cis/trans-1,4-cyclohexane dimethylene-tetrahydrofuran), 5% sodium carbonate, and 5% norethindrone; (e) 50% of poly(2,2-dioxo-cis/trans-1,4-cyclohexane dimethylene-tetrahydrofuran), 30% of sodium carbonate, and 20% of norethindrone; (f) 70% of poly(2,2-dioxo-cis/trans-1,4-cyclohexane dimethylene-tetrahydrofuran), 20% of magnesium oxide, and 10% of norethindrone; and (g) 60% of poly(2,2-dioxo-cis/trans-1,4-cyclohexane dimethylene-tetrahydrofuran), 10% of magnesium oxide, and 30% of norethindrone.

EXAMPLE 8

An implant for providing the progestational agent d-norgestrel was prepared using the procedure of the above examples as follows: 20.64 grams of the following polymer:

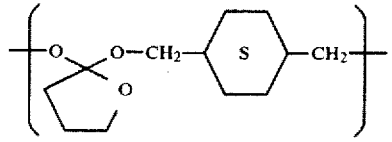

having a molecular weight of 42,473 was heated to 105° C.±2° C., on a stainless steel plate in a helium drybox, and then 0.96 grams of d-norgestrel were mixed into the polymer with a spatula. After the polymer and steroid were thoroughly mixed, 2.40 grams of dry sodium carbonate was mixed with the drug polymer mixture. Next, the three component homogenous composition was transferred to a drybox that was previously purged for two hours with dry nitrogen. Then, a mold, having an implant forming cavity, in the drybox was preheated to about 130° C. and charged with 8.2 grams of the composition. The mold was changed at 126° C. to 130° C., and a pressure of 24,000 psi applied for 15 minutes to form the implant. After the mold cooled, the implants were removed and excess flash was trimmed from the implants. The implants weighed 0.118 grams and they comprised 86% of the polymer, 10% of the modifier, and 4% of the steroid. The implants are useful for maintaining an anti-fertility state when implanted in the tissue of animals.

EXAMPLE 9

The procedure of Example 8 was repeated here, with all conditions as set forth, except that implants were made from polymers having a molecular weight of 34,285 and a molecular weight of 33,873.

EXAMPLE 10

To 26.7 grams of poly(2,2-dioxo-cis/trans-1,4-cyclohexane dimethylene tetrahydrofuran), in an Atlantic reactor with 2 mixer blades rotating at 35 rpm, and preheated to 120° C., was added 5.9 grams of d-norgestrel, and the two ingredients mixed for 15 minutes, under a nitrogen atmosphere. Next, 8.8 grams of sodium carbonate was added to the reactor, and the three ingredients blend to produce a composition having a polymer-steroid-modifier composition of 76.5%-16.8%-6.7%. The composition was manufactured in a dry environment and with anhydrous ingredients into implants by following the procedure described above.

Repeating the procedure of the example, the following implants were made: (a) an implant comprising 76.4% poly(2,2-dioxo-cis/trans-1,4-cyclohexane dimethylene tetrahydrofuran), 16.8% levo-norgestrel, and 6.8% sodium bicarbonate; (b) 76.5% poly(2,2-dioxo-cis/trans-1,4-cyclohexane dimethylene tetrahydrofuran), 16.8% levo-norgestrel, and 6.6% of magnesium oxide; (c) an implant comprising 76.6% poly(2,2-dioxo-cis/trans-1,4-cyclohexane dimethylene tetrahydrofuran), 16.8% levo-norgestrel, and 6.7% lithium hydroxide, and (d) 71.0% poly(2,2-dioxo-cis/trans-1,4-cyclohexane dimethylene tetrahydrofuran), 15.6% levo-norgestrel, and 13.4% calcium hydride.

EXAMPLE 11

The procedure of Example 10 was repeated for making an implant comprising 75% of poly(2,2-dioxo-cis/trans-1,4-cyclohexane dimethylene tetrahydrofuran), 15% d-norgestrel, and 10% magnesium oxide. The implant had a rate of release of 40 g/day of the d-norgestrel and over a 6 month period. Another implant was prepared comprising 75% of poly(2,2-dioxo-cis/trans-1,4-cyclohexane dimethylene tetrahydrofuran), 15% d-norgestrel, and 10% sodium carbonate. The implant released 40 μg/day of d-norgestrel over a 6 month period.

EXAMPLE 12

The procedure of Example 10 was followed for producing an implant comprising 80% poly(2,2-dioxo-cis/trans-1,4-cyclohexane dimethylene tetrahydrofuran), 10% insulin and 10% sodium carbonate. The polymer had a molecular weight of 36,400, the implant weighed 20 mg, and the implant released 3.2 units of insulin per day for 14 days.

EXAMPLE 13

A series of implants were prepared by heating a poly(orthoester) to 90° C.±4° C. on a Teflon TM platen in a nitrogen atmosphere. A modifier was physically mixed into the heated polymer using a stainless steel spatula for 10 minutes, and then, insulin was mixed therein for 10 to 15 minutes. The formulations were transferred to a dry box with a nitrogen atmosphere, and pressed into a 20 mil thick film with a Carver press at 190° F./20,000 psi for 5 minutes, followed by 5 minutes of cooling. Then, elliptical implants, 5 mm by 8 mm were punched from each film at room temperature in a nitrogen atmosphere. Following this procedure the following implants were prepared: (a) 80.2% poly(2,2-dioxo-cis/-trans-1,4-cyclohexane dimethylene tetrahydrofuran), 10.2% sodium carbonate, and 9.7% insulin; (b) 75.4% poly(2,2-dioxo-cis/trans-1,4-cyclohexane dimethylene tetrahydrofuran), 10.2% sodium acid carbonate, and 14.4% insulin; (c) 70% poly(2,2-dioxo-cis/trans-1,4-cyclohexane dimethylene tetrahydrofuran), 10% sodium carbonate, and 20% insulin; and (d) 60% poly(2,2-dioxo-cis/trans-1,4-cyclohexane dimethylene tetrahydrofuran), 10% magnesium oxide and 30% insulin. The polymer used for manufacturing the implant had a molecular weight of 41,000 to 43,000, the implants weighed 20 mg, and they released 8 to 20 units of insulin per day and it had a duration of between 7 and 21 days.

EXAMPLE 14

A number of antifertility implants were made comprising the following ingredients, a polymer of the following structure:

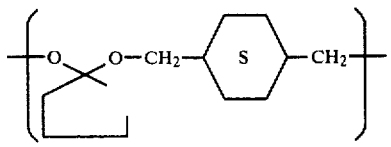

with the implant comprising the following:

| Modifier | | d-Norgestrel | Polymer | Mol wt × $10^4$ |
|---|---|---|---|---|
| 6.7% | $Na_2CO_3$ | 16.8% | 76.5% | 4.23 |
| 13.3% | $Na_2CO_3$ | 15.6% | 71.1% | 4.25 |
| 6.7% | MgO | 16.8% | 76.6% | 4.13 |
| 13.3% | MgO | 15.7% | 71.0% | 4.37 |
| 6.7% | LiOH | 16.8% | 76.5% | 3.78 |
| 13.3% | LiOH | 15.6% | 71.1% | 3.93 |
| 6.7% | $CaH_2$ | 16.8% | 76.5% | 3.61 |
| 13.3% | $CaH_2$ | 15.6% | 71.0% | 3.92 |
| 6.7% | $NaHCO_3$ | 16.8% | 76.5% | 3.62% |
| 13.3% | $NaHCO_3$ | 15.6% | 71.1% | 3.52% |

EXAMPLE 15

The procedure of Example 14 was repeated to provide the implants comprising the following ingredients, expressed as (ratio by weight):

| Modifier | | d-Norgestrel | Polymer | Release Rate µg/day Norgestrel |
|---|---|---|---|---|
| $Na_2CO_3$ | (8) | (18) | (82) | 65 ± 4 |
| $Na_2CO_3$ | (12) | (18) | (82) | 48 ± 3 |
| $Na_2CO_3$ MgO | (6) (6) | (18) | (82) | 62 ± 3 |
| MgO | (12) | (18) | (82) | 78 ± 5 |
| MgO | (16) | (18) | (82) | 53 ± 2 |

EXAMPLE 16

Compositions comprising a bioerodible polymer, a modifier, and a drug were prepared under anhydrous conditions and procedures as described in earlier examples as follows: first, a weighed amount of poly(2,2-dioxo-1,6-hexamethylene tetrahydrofuran) was heated to 150° C. in a glass beaker, and then a weighed amount of drug was mixed with the polymer. A glass rod was used to stir the polymer and the drug for producing a homogenous mixture. Next, a weighed amount of a polymer erosion rate modifier was added to the beaker, and the three ingredients stirred to produce a homogenous composition. The blending was carried out in a dry box under a nitrogen atmosphere. The following compositions were prepared by this procedure: (a) a composition comprising 90% of poly(2,2-dioxo-1,6-hexamethylene tetrahydrofuran), 10% of riboflavin, 5% sodium carbonate and 5% magnesium oxide; (b) 45% of poly(2,2-dioxo-1,6-hexamethylene tetrahydrofuran), 45% theophylline and 10% sodium carbonate; (c) 87% of poly(2,2-dioxo-1,6-hexamethylene tetrahydrofuran), 8% of hydroxyproline and 5% sodium carbonate (d) 50% of poly(2,2-dioxo-1,6-hexa-methylene tetrahydrofuran), 40% of dexamethasone and 10% of sodium carbonate; (f) 65% of poly(2,2-dioxo-1,6-hexamethylene tetrahydrofuran), 25% of fluocinolone and 10% of magnesium oxide; (g) 70% poly(2,2-dioxo-1,6-hexamethylene tetrahydrofuran), 5% ethinyl estradiol, 15% norethindrone, and 10% sodium carbonate; (h) 70% poly(2,2-dioxo-1,6-hexamethylene tetrahydrofuran), 5% mestranol, 20% norethynodrel, and 5% magnesium oxide; and (i) 70% poly(2,2-dioxo-1,6-hexamethylene tetrahydrofuran), 4% nitroglycerin, 16% lactose, and 10% sodium carbonate.

EXAMPLE 17

A drug delivery device for administering a drug at a controlled rate topically to the skin of a human for systemic circulation was made under dry conditions by pressing a composition comprising 50 parts of poly(2,2-dioxo-1,6-hexamethylene tetrahydrofuran), 50 parts of 17β-estradiol and 5 parts of sodium bicarbonate was pressed between two aluminum foil sheets into a 20 mil thick film. Then, 2 cm² topical delivery devices were punched from the foil sheets, and one sheet was peeled from the device before use. The other sheet served as a backing member for the polymer-estradiol-sodium bicarbonate composition. The composition is tacky, and when placed on the skin of a human, it sticks to the skin. A 2 cm² device in contact with the skin of a female, produced about a 50 mg per hour increase in urinary excretion of estradiol-conjugates as determined by radio immuno assay after enzymatic hydrolysis, over a normal urinary level of about 50 µg per hour. An increase of from 2 cm² to 4 cm² increased the urine level an additional 25 to 30 µg per hour. When 5 parts of sodium carbonate were used instead of 5 parts of sodium bicarbonate, the release of estradiol was then halved.

EXAMPLE 18

A bandage 2 cm by 7 cm for the management of ovulation is prepared under dry and inert conditions by coating one surface of a backing member comprising a polyethylene aluminum foil laminate, which backing member defines the bandage, with a 6 mm thick composition comprising 60 parts of poly(2,2-dioxo-1,6-hexamethylene tetrahydrofuran), 30 parts of norgestrel, 5 parts of Cab-o-sil, and 10 parts of sodium carbonate. The backing member is impermeable to the passage of steroid, and the composition is coated onto the polyethylene surface of the member. The bandage comprising the composition is sticky, and when applied to the skin releases a controlled and continuous amount of steroid over a prolonged period of time.

EXAMPLE 19

The bandage of Example 18 is prepared with the steroid in the present example comprising a member selected from the group consisting of norethindrone; a mixture of ethinyl estradiol and norethindrone; a mixture of mestranol and norethynodrel; a mixture of ethinyl estradiol and norgestrel; a mixture of mestranol and norethindrone; and a mixture of ethinyl estradiol and dimethisterone.

EXAMPLE 20

The bandage of 18 is prepared with the backing member additionally comprising a perimeter of a non-irritating pressure sensitive adhesive that surround the steroid, which adhesive is adapted for holding the steroid in intimate contact with the skin, and wherein the adhesive is selected from acrylic adhesives and urethane adhesives, and the steroid is selected from norethindrone; norgestrel; a mixture of ethinyl estradiol and norethindrone; and a mixture of ethinyl estradiol and norgestrel.

EXAMPLE 21

A series of implants were prepared by heating a poly(orthoester) to 110° C. ±5° C. in a stainless steel vessel, equipped with a stirrer, under a dry nitrogen atmosphere. A modifier and drug were blended into the molten polymer, a process which required less than two minutes. The blends were transferred to a small extruder, and they were transformed into an extrudate shaped as a long rod, 3 mm in diameter. Following this procedure, a number of implants were prepared; all containing 20% progesterone in poly(2,2-dioxo-cis/-trans-1,4-cyclohexane dimethylene-tetrahydrofuran). The remaining 80% of the implant were as follows:

| Modifier | Polymer | Mol Wt × $10^4$ |
|---|---|---|
| 2-phenylcyclopropylamine 5% | 75% | 4.8 |
| Trihydroxytriethylamine 6% | 74% | 3.6 |
| 2,4,6-trimethylpyridine 5% | 75% | 3.8 |
| 2-amino-2-hydroxymethyl-1,3-propanediol 2.5% | 77.5% | 4.0 |
| None | 80% | 3.8 |

The rods were cut into lengths between 1 cm and 2.5 cm and then placed in the subcutaneous tissue of rats. At the end of one month, at least part of all those implants which contained modifiers were found at the site of implantation. The implant which did not contain any erosion rate modifier was not visible on macroscopic examination at the site of implantation. The experiment indicates the amine modifiers retard the rate of erosion and drug delivery from the implants.

EXAMPLE 22

The procedure of Example 13 was followed for producing an implant comprising 80% poly(2,2-dioxo-cis/-trans-1,4-cyclohexane dimethylene-tetrahydrofuran), 16% hydrocortisone, and 4% of a rate controlling modifier. The initial molecular weight of the polymer was 37,000. In vitro release studies were performed in 0.1 molar sodium phosphate buffers. The results for a series of modifiers and the approximate time at which greater than 90% of the drug was released are as follows:

| Modifier | Time |
|---|---|
| $NaH_2PO_4$ | <3 days |
| $Na_2HPO_4$ | 5 days |
| $Na_3PO_4$ | 17 days |
| $MgSO_4$ | 10 days |
| $NaHCO_3$ | 8 days |
| $Na_2CO_3$ | >20 days |
| $Na_2CO_3$ + CaO | >20 days |

EXAMPLE 23

A drug delivery device for administering a drug at a controlled rate into the ano-rectal passageway was made by formulating 50 parts of theophylline, 10-parts of diethylamine and 40 parts of poly(2,2-dioxo-1,6-hexamethylene tetrahydrofuran) in a dry nitrogen atmosphere. A measured sample was placed in the passageway of dogs and plasma samples were taken at 4 hour intervals. The results indicated that 90% of the drug released from the device made with the modifier, was absorbed into the blood system during the first 18 hours after administration. When the rate accelerating modifier was omitted from the device, about 50% of the drug was absorbed during the same time period.

EXAMPLE 24

The procedure of Example 22 was followed for producing an ocular insert comprising 80% poly(2,2-dioxo-cis/trans-1,4-cyclohexane dimethylene titrahydrofuran), 16% prednisolone acetate and 4% sodium carbonate. The ocular implant was placed in one eye of a test host and it had a prolonged life of 17 days. An ocular implant made without the sodium carbonate modifier was placed in the other eye of the host, and it had a life of about two days duration.

EXAMPLE 25

A drug delivery device for administering a drug at a controlled rate into a vagina is made by formulating 50 parts of progesterone, 10 parts of diethylamine and 40 parts of poly(2,2-dioxo-1,6-hexamethylene tetrahydrofuran) in a dry nitrogen atmosphere by following the fabrication procedures as described above. The device when inserted in the vagina, administers the steroid over a prolonged period of time.

EXAMPLE 26

A drug delivery device for administering an anti-ulcer drug to the gastrointestinal tract is made by formulating 50 parts of mepyramine, 10 parts of sodium carbonate and 40 parts of poly(2,2-dioxo-cis/trans-1,4-cyclohexane dimethylene tetrahydrofuran) in a dry inert atmosphere by following the above procedures. The device when administered orally released the drug over time.

EXAMPLE 27

A series of drug delivery devices are prepared by following the above procedures and using the above erosion rate modifiers, with the polymer in the present example a member selected from the groups as follows: poly(1,1-dioxo-cis/trans-1,4-cyclohexane dimethylene cyclopentane; poly(1,1-dioxo-cis/trans-1,4-cyclohexane dimethylene cyclohexane; poly(1,1-dioxo-1,6-hexamethylene cyclopentane); poly(1,1-dioxo-1,6-hexamethylene cyclopentane; and poly(1,1-dioxo-1,10-decamethylene cyclopentane).

Although the foregoing invention has been described in detail, both by way of discussion and by way of illustration of presently preferred embodiments and examples for the purpose of clarity of understanding the invention, it will be understood that changes and modifications may be made within the scope of the invention.

I claim:

1. A device for delivering a beneficial drug at a controlled rate over a prolonged period, said device shaped, sized and adapted for delivering a drug to an animal environment of use, the device comprising: (A) an erodible released rate controlling polymer of the formula:

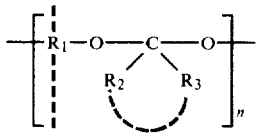

wherein (I) $R_1$ is a member selected from the group consisting of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, an alkenyl of 2 to 7 carbons, and an alkylene of 1 to 10 carbons; cycloalkylene of 4 to 7 carbons; cycloalkenylene of 4 to 7 carbons substituted with an alkyl of 1 to 7 carbons, an alkoxy of 1 to 7 carbons, alkenyl of 2 to 7 carbons, and an alkylene of 1 to 10 carbons; arylene of 6 to 12 carbons; arylene of 6 to 12 carbons substituted with an alkyl of 1 to 7 carbons, alkyloxy of 1 to 7 carbons, alkenyl of 2 to 7 carbons, and alkylene of 1 to 10 carbons; wherein (II) $R_2$ and $R_3$ are selected from the grop consisting of alkyl of 1 to 7 carbons, alkenyl of 2 to 7 carbons, aryl or 6 to 12 carbons, an oxygen atom covalently bonded to the dioxycarbon atom, and when an oxygen atom $R_2$ and $R_3$ are a member selected from the group consisting of alkyloxy of 1 to 7 carbons; alkenyloxy of 2 to 7 carbons; and aryloxy of 6 to 12 carbons; and when only one of $R_2$ and $R_3$ is selected from said member the other $R_2$ and $R_3$ is selected from the group consisting of alkyl of 1 to 7 carbons; alkenyl of 2 to 7 carbons; and aryl of 6 to 12 carbons; wherein (III) $R_2$ and $R_3$ are intramolecularly covalently bonded to each other and to the same dioxycarbon atom, with at least one of $R_2$ and $R_3$ a ring oxygen atom forming a heterocyclic ring of 5 to 8 carbon and oxygen atoms when $R_2$ and $R_3$ are selected from the group consisting of alkylene of 2 to 6 carbons; alkenylene of 2 to 6 carbons; alkyleneoxy of 2 to 6 carbons; alkenyleneoxy of 2 to 6 carbons; alkylenedioxy of 2 to 5 carbons; alkenylenedieoxy of 2 to 5 carbons; oxa; and a heterocyclic ring of 5 to 8 carbon and oxygen atoms substituted with an alkyl of 1 to 7 carbons, an alkyloxy of 1 to 7 carbons, an alkenyl of 2 to 7 carbons, and an alkenyloxy of 2 to 7 carbons; wherein (IV) $R_2$ and $R_3$ are intramolecularly covalently bonded to each other and to the same dioxycarbon atom with at least one of $R_2$ and $R_3$ is a ring oxygen atom forming a fused polycyclic ring of 8 to 12 carbon and oxygen atoms when $R_2$ and $R_3$ are a member selected from the group consisting of aralkylene of 8 to 12 carbons; aralkenylene of 8 to 12 carbons, aryloxy of 8 to 12 carbons; aralkyleneoxy of 8 to 12 carbons; aralkenyleneoxy of 8 to 12 carbons, aralkylenedioxy of 8 to 12 carbons; aralkenylenedioxy of 8 to 12 carbons; oxa; and a fused polycyclic ring of 8 to 12 carbon and oxygen atoms substituted with an alkyl of 1 to 7 carbons, an alkyloxy of 1 to 7 carbons, an alkenyl of 2 to 7 carbons and an alkenyloxy of 2 to 7 carbons; wherein (V) $R_2$ and $R_3$ are intramolecularly covalently bonded to each other and to the same dioxycarbon atom to form a 5 to 6 member carbocyclic ring; (B) a beneficial drug in the device; (C) an erosion rate modifier in the device in an amount that effects the period of time the device erodes and effects the amount of drug released as the device erodes over time; and wherein n is greater than 10.

2. The device for delivering drug at a controlled rate over a prolonged period of time according to claim 1 wherein erosion rate modifier decrease the rate of erosion of the polymer over time.

3. The device for delivering drug at a controlled rate over a prolonged period of time according to claim 1 wherein the erosion rate modifier increase the rate of erosion of polymer over time.

4. The device for delivering drug at a controlled rate over a prolonged period of time according to claim 1 wherein the erosion rate modifier controls the environment within the device by maintaining a relative pH of at least 7 when the device is in use.

5. The device for delivering drug at a controlled rate over a prolonged period of time according to claim 1 wherein the erosion rate modifier controls the environment within the device by maintaining a relative pH of less than 7 when the device is in use.

6. The device for delivering drug at a controlled rate over a prolonged period of time according to claim 1 wherein the erosion rate modifier is a member selected from the group consisting of metal oxides, salts of electronegative nonmetal oxides, hydrides, metals, hydroxides, amines, organic acids, inorganic acids, monobasic acid salts, polybasic acid salts, and hydroxides of nonmetals.

7. The device for delivering drug at a controlled rate over a prolonged period of time according to claim 1 wherein the erosion rate modifier is a member selected from the group consisting of aluminum oxide, calcium oxide, lithium oxide, magnesium oxide, manganese oxide, potassium oxide, and sodium oxide.

8. The device for delivering drug at a controlled rate over a prolonged period of time according to claim 1 wherein the erosion rate modifier is a member selected from the group consisting of calcium carbonate, lithium carbonate, magnesium carbonate, sodium acid carbonate, potassium carbonate, sodium carbonate, calcium phosphate, lithium phosphate, disodium hydrogen phosphate, magnesium phosphate, potassium dihydrogen phosphate, manganese phosphate, potassium phosphate, sodium phosphate, sodium hydrogen phosphate, calcium sulfite, lithium sulfite, magnesium sulfite, potassium sulfite, sodium sulfite, lithium sulfate, potassium sulfate, and sodium sulfate.

9. The device for delivering drug at a controlled rate over a prolonged period of tie according to claim 1 wherein the erosion rate modifier is a member selected from the group consisting of aluminum, calcium, lithium, magnesium, potassium, and sodium.

10. The device for delivering drug at a controlled rate over a prolonged period of time according to claim 1 wherein the erosion rate modifier is a member selected from the group consisting of aluminum hydride, calcium hydride, lithium hydride, magnesium hydride, potassium hydride, and sodium hydride.

11. The device for delivering drug at a controlled rate over a prolonged period of time according to claim 1 wherein the erosion rate modifier is a member selected from the group consisting of aluminum hydroxide, barium hydroxide, calcium hydroxide, lithium hydroxide, magnesium hydroxide, potassium hydroxide, and sodium hydroxide.

12. The device for delivering drug at a controlled rate over a prolonged period of time according to claim 1 wherein the erosion rate modifier is a member selected from the group consisting of amygladic acid, adipic acid, boric acid, citric acid, fumaric acid, itaconic acid, lactic acid, malic acid, maleic acid, mesaconic acid, oxalic acid, phthalic acid, phosphoric acid, succinic acid, sulfamic acid, tartaric acid, glycine, amino acid, stannic chloride, and mixtures thereof.

13. The device for delivering drug at a controlled rate over a prolonged period of time according to claim 1 wherein the erosion rate modifier is a member selected from the group consisting of trimethylamine, triethylamine, tridecylamine, hydroxylamine, propylamine, ethylenediamine, phenylcyclopropylamine, trihydroxytyriethylamine, 2,4,6-trimethylpyridine and 2-hydroxy-1-aminopropane.

14. The device for delivering drug at a controlled rate over a prolonged period of time according to claim 1 wherein the erosion rate modifier is a member selected from the group consisting of potassium tetraoxalate, potassium hydrogen tartrate, potassium hydrogen phthalate, sodium tetraoxalate, sodium hydrogen tartrate, sodium hydrogen phthalate, potassium dihydrogen citrate, sodium dihydrogen citrate, sodium acetate, sodium p-toluenesulfonate, and p-toluenesulfonic acid.

15. A device for delivering a beneficial drug at a controlled rate over a prolonged period of time, which device is sized, shaped and adapted for delivering a drug to an animal, the device comprising (a) a polymer of the formula:

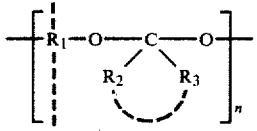

wherein $R_1$ is a member selected from the group consisting of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, an alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, alkenyl of 2 to 7 carbons, and an alkylene of 1 to 10 carbons; arylene of 6 to 12 carbons; arylene of 6 to 12 carbons substituted with an alkyl of 1 to 7 carbons, alkyloxy of 1 to 7 carbons, an alkenyl of 2 to 7 carbons and an alkylene of 1 to 10 carbons; wherein $R_2$ and $R_3$ are taken together to form a 5 to 8 member heterocycyclic ring selected from the group consisting of dioxolanyl; dioxanyl; dioxepanyl; dioxocanyl; dioxonanyl; tetrahydrofuranyl; dihydrofuranyl; furyl; pyranyl; ocanyl; and oxepanyl; (b) an erosion rate modifier dispersed in the device, said erosion rate modifier is a member selected from inorganic metals and compounds that decrease rate of erosion of the polymer, and inorganic metals and compounds that increase the rate of erosion of the polymer; (c) a dosage unit amount of a drug in the device, said drug a member selected from the group consisting of locally and systemically acting drugs; and wherein n is greater than 10.

16. The device for delivering the beneficial drug over a period of time according to claim 15 wherein the device is sized and shaped as an implant.

17. The device for delivering the beneficial drug over a period of time according to claim 15 wherein the device is sizes and shaped as a strip.

18. The device for delivering the beneficial drug over a period of time according to claim 15 wherein the animal is a human.

19. The device for delivering the beneficial drug over a period of time according to claim 15 wherein the device is sized and shaped as a suppository.

20. The device for delivering the beneficial drug over a period of time according to claim 15 wherein the polymer is poly(2,2-dioxo-cis/trans-1,4-cyclohexane dimethylene tetrahydrofuran).

21. The device for delivering the beneficial drug over a period of time according to claim 15 wherein the drug is poly(2,2-dioxo-1,6-hexamethylene tetrahydrofuran).

22. A device for delivering a beneficial drug at a controlled rate over a period of time, wherein the device is sized and shaped for delivering a drug to a warm-blooded animal, said device comprising (a) a polymer of the formula:

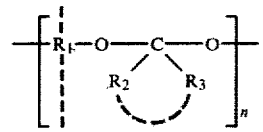

wherein $R_1$ is a member selected from the group consisting of divalent, trivalent, and tetravalet radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, an alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, alkenyl of 2 to 7 carbons, and an alkylene of 1 to 10 carbons; arylene of 6 to 12 carbons; arylene of 6 to 12 carbons substituted with ann alkyl of 1 to 7 carbons, alkyloxy of 1 to 7 carbons, alkenyl of 2 to 7 carbons, and alkylene of 1 to 10 carbons; $R_2$ and $R_3$ are taken together defining a heterocyclic ring with at least one of $R_2$ and $R_3$ a ring forming oxygen atom, with the heterocyclic ring a member selected from the group consisting of dioxolanyl; dioxanyl; dioxepanyl; dioxocanyl; dioxonanyl; tetrahydrofuranyl; dihydrofuranyl; furyl; pyranyl; ocanyl; and oxepanyl; (b) an erosion rate modifier in the polymer, said erosion rate modifier selected from the group consisting of metals and inorganic compounds that decrease the rate of erosion of the polymer, and metals and inorganic compounds that increase the erosion rate of the polymer; (c) a drug in the polymer selected from the group consisting of hypoglycemic, and hormonal drugs; and n is greater than 10.

23. The device for delivering the beneficial drug at a controlled rate over a period of time according to claim 20 wherein the polymer is defined by the following structural formula:

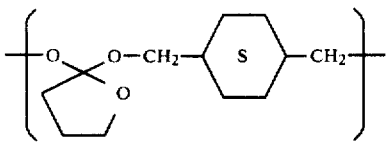

wherein the hormone is a member selected from the group consisting of cortical, androgenic, estrogenic and progestational hormones; and wherein the erosion rate modifier is selected from the group consisting of metal oxides, salts of nonmetal oxides, hydrides, hydroxides, acids, monobasic, and polybasic salts, acidic salts, amines and mixtures thereof.

24. The device for delivering the beneficial drug at a controlled rate according to claim 23 wherein the hormone is a member selected from the group consisting of aldesterone, desoxycorticosterone, cortisone, hydrocortisone, prednisone, prednisolone, triamcinolone, paramethasone, dexamethasone, fludrocortisone acetate, flurandrenolone acetonide, betamethasone benzoate, dexamethasone phosphate, methyl prednisolone, prednisolone acetate, and triamcinolone acetonide.

25. The device for delivering the beneficial drug at a controlled rate according to claim 23 wherein the hormone is a member selected from the group consisting of estradiol, 17β-estradiol, 3-benzoate estradiol, 3-acetate estradiol, 17-acetate estradiol, 17β-propionate estradiol, 17β-heptanoate estradiol, 17β-undecanoate estradiol, 17β-valerate estradiol, 3-methyl ether estradiol, 3,17β-diacetate estradiol, 3,17β-dipropionate estradiol, hemisuccinate estradiol, 17β-cypionate estradiol, 17β-estradiol disodium diphosphate, estriol, estrone, ethinyl estradiol, estrazinol, estrofurate, quinestrol, and mixtures thereof.

26. The device for delivering the beneficial drug at a controlled rate according to claim 23 wherein the hormone is a member selected from the group consisting of progesterone, preganediol, algestone acetophenide, azacosterol, chlormadinone acetate, dyhdrogesterone, ethisterone, hydroxyprogesterone, medrogesterone, medroxyprogesterone, megestrol acetate, melengestrol acetate, allylestrenol, ethynodiol diacetate, lynestrenol, norethindrone, norethindrone acetate, norethynodrel, norgesterone, norgestrel, norgestrienone, norvinisterone, oxogestone, quingestrone, quingestanol acetate, tigestol, and mixtures thereof.

27. The device for delivering the beneficial drug at a controlled rate according to claim 23 wherein the hormone is a member selected from the group consisting of testosterone, testosterone propionate, methyl testosterone, mesterolone, fluoxymesterone, methandriol, methandrostenolone, methenolone enanthate, nandrolone, norethandrolone, oxymetholone, stanozolol, zeranol, and mixtures thereof.

28. The device for the delivery of the beneficial drug at a controlled rate according to claim 23 wherein the hypoglycemic drug is a member selected from the group consisting of insulin, zinc insulin, dalanated insulin, zinc globin insulin, isophane insulin, protamine insulin, extended zinc insulin, sulfonylureas, acetohexamide, glypinamide, chlorpropamide, tolazamide, tolbutamide, phenformin, and mixtures thereof.

29. The device for delivering the beneficial drug at a controlled rate according to claim 23 wherein the erosion rate modifier is a member selected from the group consisting of calcium oxide, calcium dibasic phosphate, calcium phosphate, magnesium carbonate, sodium carbonate, sodium bicarbonate, magnesium oxide, and mixtures thereof.

30. A bioerodible, drug delivery implant comprising 70% by weight of poly(2,2-dioxo-cis/trans-1,4-cyclohexane dimethylene tetrahydrofuran), 20% by weight of sodium carbonate, and 10% by weight of d-norethisterone.

31. A bioerodible, drug delivery implant comprising 70% by weight of poly(2,2-dioxo-cis/trans-1,4-cyclohexane dimethylene tetrahydrofuran), 10% by weight of calcium oxide, and 20% by weight of norethindrone.

32. A bioerodible, drug delivery implant comprising 70% by weight of poly(2,2-dioxo-cis/trans-1,4-cyclohexane dimethylene tetrahydrofuran), 5% by weight of calcium oxide, and 25% by weight of norethindrone.

33. A bioerodible, drug delivery implant comprising 75% by weight of poly(2,2-dioxo-cis/trans-1,4-cyclohexane dimethylene tetrahydrofuran), 5% by weight of calcium oxide, and 20% by weight of norethindrone.

34. A bioerodible, drug delivery implant comprising 50 to 90% of poly(2,2-dioxo-cis/trans-1,4-cyclohexane dimethylene tetrahydrofuran), 5 to 30% of a member selected from the group consisting of sodium carbonate, calcium oxide, magnesium oxide and mixtures thereof, and 5 to 30% of norethindrone.

35. The bioerodible, drug delivery implant according to claim 33 wherein implant comprises 70% of poly(2,2-dioxo-cis/trans-1,4-cyclohexane dimethylene tetrahydrofuran), 10% of sodium carbonate, and 20% of norethindrone.

36. The bioerodible, drug delivery implant according to claim 33 wherein the implant comprises 70% of poly(2,2-dioxo-cis/trans-1,4-cyclohexane dimethylene tetrahydrofuran), 20% of sodium carbonate, and 10% of norethindrone.

37. The bioerodible, drug delivery implant according to claim 33 wherein the implant comprises 55% of poly(2,2-dioxo-cis/trans-1,4-cyclohexane dimethylene tetrahydrofuran), 20% of sodium carbonate, and 25% of norethindrone.

38. The bioerodible, drug delivery implant according to claim 33 wherein the implant comprises 50% of poly(2,2-dioxo-cis/trans-1,4-cyclohexane dimethylene tetrahydrofuran), 20% of sodium carbonate, and 30% of norethindrone.

39. The bioerodible drug delivery implant according to claim 33 wherein the implant comprises 90% of poly(2,2-dioxo-cis/trans-1,4-cyclohexane dimethylene tetrahydrofuran), 5% of sodium carbonate, and 5% of norethindrone.

40. The bioerodible drug delivery implant according to claim 33 wherein the implant comprises 50% of poly(2,2-dioxo-cis/trans-1,4-cyclohexane dimethylene tetrahydrofuran), 30% of sodium carbonate, and 20% of norethindrone.

41. The bioerodible drug delivery implant according to claim 33 wherein the implant comprises 70% of poly(2,2-dioxo-cis/trans-1,4-cyclohexane dimethylene tetrahydrofuran), 20% of magnesium oxide and 10% of norethindrone.

42. The bioerodible drug delivery implant according to claim 33 wherein the implant comprises 60% of poly(2,2-dioxo-cis/trans-1,4-cyclohexane dimethylene tetrahydrofuran), 10% of magnesium oxide, and 30% norethindrone.

43. A bioerodible, drug delivery implant comprising 50 to 90% of poly(2,2-dioxo-cis/trans-1,4-cyclohexane dimethylene tetrahydrofuran), 5 to 30% of a member selected from the group consisting of sodium carbonate, sodium bicarbonate, magnesium oxide, lithium hydroxide and calcium hydride, and from 4 to 30% of norgestrel.

44. The bioerodible drug delivery implant according to claim 43 wherein the implant comprises 86% of poly(2,2-dioxo-cis/trans-1,4-cyclohexane dimethylene tetrahydrofuran), 10% of sodium carbonate, and 4% of norgestrel.

45. The bioerodible drug delivery implant according to claim 43 wherein the implant comprises 76.5% of poly(2,2-dioxo-cis/trans-1,4-cyclohexane dimethylene tetrahydrofuran), 16.8% of sodium carbonate, and 6.7% of norgestrel.

46. The bioerodible drug delivery implant according to claim 43 wherein the implant comprises 76.4% of poly(2,2-dioxo-cis/trans-1,4-cyclohexane dimethylene tetrahydrofuran), 16.8% of norgestrel and 6.8% of sodium carbonate.

47. The bioerodible drug delivery implant according to claim 43 wherein the implant comprises 76.5% of poly(2,2-dioxo-cis/trans-1,4-cyclohexane dimethylene tetrahydrofuran), 16.8% of norgestrel, and 6.7% of magnesium oxide.

48. The bioerodible drug delivery implant according to claim 43 wherein the implant comprises 75% of poly(2,2-dioxo-cis/trans-1,4-cyclohexane dimethylene tetrahydrofuran), 15% of norgestrel, and 10% of magnesium oxide.

49. The bioerodible drug delivery implant according to claim 43 wherein the implant comprises 75% of poly(2,2-dioxo-cis/trans-1,4-cyclohexane dimethylene tetrahydrofuran), 15% of norgestrel and 10% of sodium carbonate.

50. The bioerodible drug delivery implant according to claim 43 wherein the implant comprises 71.1% of poly(2,2-dioxo-cis/trans-1,4-cyclohexane dimethylene tetrahydrofuran), 15.6% of norgestrel, and 13.3% of sodium carbonate.

51. The bioerodible drug delivery implant according to claim 43 wherein the implant comprises 71.0% of poly(2,2-dioxo-cis/trans-1,4-cyclohexane dimethylene tetrahydrofuran), 15.7% of norgestrel and 13.3% of magnesium oxide.

52. The bioerodible drug delivery implant according to claim 43 wherein the implant comprises 76.5% of poly(2,2-dioxo-cis/trans-1,4-cyclohexane dimethylene tetrahydrofuran), 16.8% of norgestrel and 6.7% of sodium bicarbonate.

53. The bioerodible drug delivery implant according to claim 43 wherein the implant comprises 71.1% of poly(2,2-dioxo-cis/trans-1,4-cyclohexane dimethylene tetrahydrofuran), 15.6% of norgestrel and 13.3% of sodium bicarbonate.

54. The bioerodible drug delivery implant comprising 50 to 90% of poly(2,2-dioxo-cis/trans-1,4-cyclohexane dimethylene tetrahydrofuran), 5 to 30% of a hypoglycemic drug, and 5 to 30% of a member selected from the group consisting of sodium carbonate, sodium bicarbonate, magnesium oxide, lithium hydroxide, and calcium hydride.

55. A bioerodible drug delivery implant comprising 50 to 90% of poly(2,2-dioxo-cis/trans-1,4-cyclohexane dimethylene tetrahydrofuran), about 5 to 30% of insulin, and about 5 to 30% of an erosion rate modifier selected from the group consisting of sodium carbonate, sodium bicarbonate and magnesium oxide.

56. The bioerodible drug delivery implant according to claim 55 wherein the implant comprises 80% of poly(2,2-dioxo-cis/trans-1,4-cyclohexane dimethylene tetrahydrofuran), 10% of insulin and 10% of sodium carbonate.

57. The bioerodible drug delivery implant according to claim 55 wherein the implant comprises about 80% of poly(2,2-dioxo-cis/trans-1,4-cyclohexane dimethylene tetrahydrofuran), 10% of sodium carbonate and 10% of insulin.

58. The bioerodible drug delivery implant according to claim 55 wherein the implant comprises about 75% of poly(2,2-dioxo-cis/trans-1,4-cyclohexane dimethylene tetrahydrofuran), 10% of sodium bicarbonate, and about 15% of insulin.

59. The bioerodible drug delivery implant according to claim 55 wherein the implant comprises 70% of poly(2,2dioxo-cis/trans-1,4-cyclohexane dimethylene tetrahydrofuran), 10% of sodium carbonate, and 20% insulin.

60. The bioerodible drug delivery implant according to claim 55 wherein the implant comprises about 60% of poly(2,2-dioxo-cis/trans-1,4-cyclohexane dimethylene tetrahydrofuran), about 10% of magnesium oxide, and about 30% of insulin.

61. The bioerodible drug delivery implant according to claim 55 wherein the implant delivers 8 to 20 units of insulin per day for up to 14 days.

62. A topical device for delivering a drug to the skin and mucosa, the device comprising a backing member supporting on one surface thereof, a composition comprising poly(2,2-dioxo-cis/trans-1,4-cyclohexane dimethylene tetrahydrofuran), an erosion rate modifier selected from the group consisting of sodium carbonate, sodium bicarbonate and magnesium oxide, and a steroid selected from the group consisting of norgestrel, norethindrone, estradiol, ethinyl estradiol, mestranol, dimethisterone, and mixtures thereof.

63. A topical device for delivering a drug to the skin and mucosa, the device comprising a backing member supporting on one surface thereof a composition comprising poly(2,2-dioxo-cis/trans-1,4-cyclohexane dimethylene tetrahydrofuran), nitroglycerin, lactose and an erosion rate modifier selected from the group consisting of sodium carbonate, sodium bicarbonate and magnesium oxide.

64. A composition of matter comprising a bioerodible polymer of the general structure:

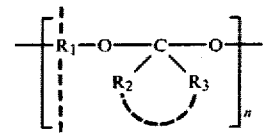

wherein $R_1$ is a member selected from the group consisting of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons; alkoxy of 1 to 7 carbons, an alkenyl of 2 to 7 carbons, and an alkylene of 1 to 10 carbons; cycloalkenylene of 4 to 7 carbons; cycloalkylene of 4 to 7 carbons substituted with an alkyl of 1 to 7 carbons, an alkoxy of 1 to 7 carbons, an alkenyl of 2 to 7 carbons, and an alkylene of 1 to 10 carbons; arylene of 6 to 12 carbons; arylene of 6 to 12 carbons substituted with an alkyl of 1 to 7 carbons, alkoxy of 1 to 7 carbons, an alkenyl of 2 to 7 carbons, and an alkylene of 1 to 10 carbons; wherein $R_2$ and $R_3$ are taken together to form a 5 to 8 member heterocyclic ring selected from the group consisting of dioxolanyl; dioxanyl; dioxepanyl; dioxonanyl; tetrahydrofuranyl; dihydrofuranyl; furyl; pyranyl; ocanyl; and oxepanyl; and an erosion rate modifier for the polymer, said modifier a member selected from the group consisting of aluminum oxide, calcium oxide, lithium oxide, magnesium oxide, potassium oxide, and sodium oxide.

65. A composition of matter comprising a bioerodible polymer of the general structure:

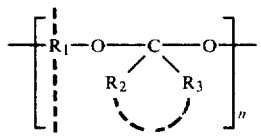

wherein $R_1$ is a member selected from the group consisting of divalent, trivalent and tetravalent radicals consisting of alylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, an alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, an alkenyl of 2 to 7 carbons, and an alkylene of 1 to 10 carbons; arylene of 6 to 12 carbons; arylene of 6 to 12 carbons substituted with an alkyl of 1 to 7 carbons, alkoxy of 1 to 7 carbons, an alkenyl of 2 to 7 carbons, and an alkylene of 1 to 10 carbons; wherein $R_2$ and $R_3$ are taken together to form a 5 to 8 member heterocyclic ring with at least one of $R_2$ and $R_3$ a ring oxygen atom with the ring selected from the group consisting of dioxolanyl, dioxanyl, dioxepanyl, dioxonanyl, tetrahydrofuranyl, dihydrofuranyl, furyl, pyranyl, ocanyl, and oxepanyl; an erosion rate modifier for the polymer, said modifier a member selected from the group consisting of calcium carbonate, lithium carbonate, magnesium carbonate, potassium carbonate, sodium carbonate, sodium bicarbonate, potassium bicarbonate, calcium phosphate, lithium phosphate, magnesium phosphate, potassium phosphate, sodium phosphate, calcium sulfite, lithium sulfite, magnesium sulfite, potassium sulfite, sodium sulfite, lithium sulfate, potassium sulfate, and sodium sulfate; and a dosage unit amount of a beneficial drug that is released at a controlled rate as the bioerodible polymer bioerodes over time.

66. A composition of matter comprising a bioerodible polymer of the general structure:

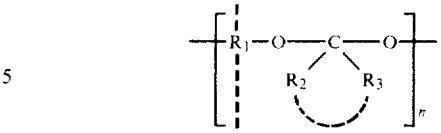

wherein $R_1$ is a member selected from the group consisting of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, an alkenyl of 2 to 7 carbons, and an alkylene of 1 to 10 carbons; arylene of 6 to 12 carbons; arylene of 6 to 12 carbons substituted with an alkyl of 1 to 7 carbons, alkoxy of 1 to 7 carbons, alkenyl of 2 to 7 carbons and alkylene of 1 to 10 carbons; wherein $R_2$ and $R_3$ are taken together to form a 5 to 8 member heterocyclic ring with at least one of $R_2$ and $R_3$ a ring oxygen atom, with the ring selected from the group consisting of dioxolanyl, dioxanyl, dioxepanyl, dioxonanyl, tetrahydrofuranyl, dihydrofuranyl, furyl, ocanyl, and oxepanyl; and n is greater than 10, and an erosion rate modifier selected from the group of acids consisting of amygladic, adipic, boric, citric, amino, fumaric, itaconic, latic, malic, maleic, mesaconic, oxalic, phthalic, phosphoric, succinic, sulfamic, and tartaric, which erosion rate modifier is present in an effective amount and cooperates with the polymer for regulating the rate of erosion of the polymer; and a dosage unit amount of drug for release in an effective amount over time.

67. A composition of matter comprising a bioerodible polymer of the general structure:

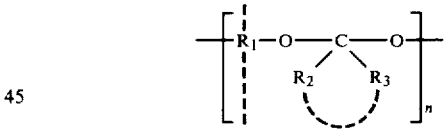

wherein $R_1$ is a member selected from the group consisting of divalent, trivalent, and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons. alkenyl of 2 to 7 carbons, and alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, an alkenyl of 2 to 7 carbons, and alkylene of 1 to 10 carbons; arylene of 6 to 12 carbons; arylene of 6 to 12 carbons substituted with an alkyl of 1 to 7 carbons, alkoxy of 1 to 7 carbons, alkenyl of 2 to 7 carbons, and alkylene of 1 to 10 carbons; wherein $R_2$ and $R_3$ are taken together to form a 5 to 8 member heterocyclic ring with at least one of $R_2$ and $R_3$ a ring oxygen atom, said ring selected from the group consisting of dioxolanyl, dioxanyl, dioxepanyl, dioxonanyl, tetrahydrofuranyl, dihydrofuranyl, furyl, ocanyl, and oxepanyl; and n is greater than 10; and an erosion rate modifier selected from the group consisting of potassium tetraoxalate, potassium hydrogen tartrate, potassium hydrogen phthalate, sodium tetraoxalate, sodium hydrogen tartrate, sodium hydrogen phthalate, a mixture of sodium tetraoxalate and sodium acid carbonate, a mixture of potassium dihydrogen phosphate and sodium hydrogen phosphate, potassium dihydrogen citrate, citric acid and sodium acetate, and glycine and citric acid.

68. A method for administering a contraceptive steroid to a warm-blooded animal, which method comprises:
  A. Admitting to the animal a bioerodible device, the device comprising:
    1. a bioerodible polymer of the general structure:

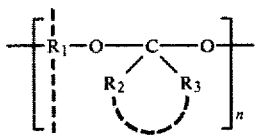

wherein $R_1$ is a member selected from the group consisting of divalent, trivalent, and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, alkenyl of 2 to 7 carbons, and alkylene of 1 to 10 carbons; cycloalkylene of 4 to 7 carbons; cycloalkylene of 4 to 7 carbons substituted with an alkyl of 1 to 7 carbons, an alkoxy of 1 to 7 carbons, alkenyl of 2 to 7 carbons, and alkylene of 1 to 10 carbons; arylene of 6 to 12 carbons; arylene of 6 to 12 carbons substituted with an alkyl of 1 to 7 carbons, alkoxy of 1 to 7 carbons, alkenyl of 2 to 7 carbons and alkylene of 1 to 10 carbons; wherein $R_2$ and $R_3$ are taken together to form a 5 to 8 member heterocyclic ring with at least one of $R_2$ and $R_3$ a ring oxygen atom, said ring selected from the group consisting of dioxolanyl, dioxanyl, dioxepanyl, dioxonanyl, tetrahydrofuranyl, dihydrofuranyl, furyl, ocanyl, and oxepanyl; and n is greater than 10;
    2. an effective amount of an erosion rate modifier that assists in regulating the rate of erosion of the polymer over time mixed with the polymer;
    3. a dosage amount of a contraceptive steroid mixed with the polymer; and,
  B. administering a contraceptively effective amount of the steroid to the animal by the device bioeroding at a controlled rate over a prolonged period of time.

69. The method for administering the contraceptive steroid to the animal over time according to claim 68 wherein the steroid is a member selected from the group consisting essentially of testosterone, testosterone propionate and methyl testosterone.

70. A method for administering the contraceptive steroid to the animal over time according to claim 68 wherein the steroid is a member selected from the group consisting of androgenic, estrogenic and progestational steroids, and mixtures thereof.

71. The method for administering the contraceptive steroid to the animal over time according to claim 68 wherein the steroid is a member selected from the group consisting of ethinyl estradiol, mestranol, norethindrone, ethynodiol diacetate, norethynodrel, norethindrone acetate, norgestrel, progesterone, and mixtures thereof.

72. The method for administering the contraceptive steroid to the animal over time according to claim 68 wherein the polymer has the formula:

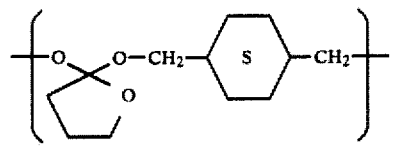

wherein the erosion rate modifier is sodium carbonate, the steroid is norethindrone, the animal is a human, and the device is sized and shaped as an implant.

73. A method for administering the contraceptive steroid to the animal over time according to claim 68 wherein

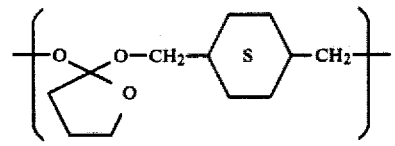

wherein the erosion rate modifier is magnesium oxide, the steroid is norethindrone, the animal is a human, and the device is sized and shaped as an implant.

74. The method for administering the contraceptive steroid to the animal over time according to claim 68 wherein the polymer has the formula:

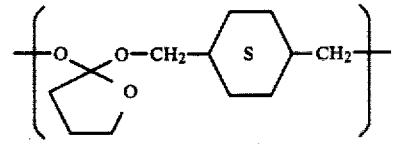

wherein the erosion rate modifier is sodium carbonate, the steroid is norgestrel, the animal is a human, and the device is sized and shaped as an implant.

75. The method for administering the contraceptive steroid to the animal over time according to claim 68 wherein the polymer has the formula:

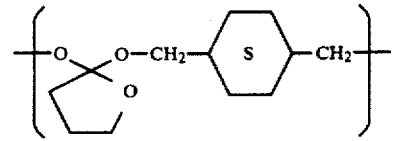

wherein the erosion rate modifier is magnesium oxide, the steroid is norgestrel, the animal is a human, and the device is sized and shaped as an implant.

76. A method for administering a beneficially effective amount of a steroid to a warm-blooded animal, which method comprises:
  A. placing on the animal a bioerodible device, the device comprising:
    1. A bioerodible polymer of the following structure:

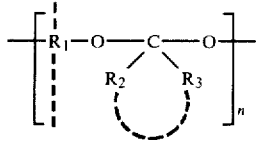

wherein $R_1$ is a member selected from the group consisting of divalent, trivalent, and tetravalent radicals consisting of alkylene of 1 to 10 carbons; alkenylene of 2 to 10 carbons; and alkyleneoxy of 2 to 6 carbons; wherein $R_2$ and $R_3$ are taken together to form a 5 to 8 member heterocyclic ring with at least one of $R_2$ and $R_3$ a ring forming oxygen atom, said ring selected from the group consisting of dioxolanyl, dioxanyl, dioxepanyl, dioxonanyl, tetrahydrofuranyl, dihydrofuranyl, furyl, ocanyl and oxepanyl, and n is greater than 10;
2. an erosion rate modifier in an effective amount that assists in regulating the rate of erosion of the bioerodible polymer over time mixed with the polymer;
3. a steroid selected from the group consisting of cortical, androgenic, estrogenic, and progestational steroids, and mixtures thereof mixed with the polymer; and B. administering an effective amount of the steroid to the animal by the device bioeroding at a controlled rate over a prolonged period of time.

77. The method for administering a beneficially effective amount of the steroid to the animal over time according to claim 76 wherein the androgenic steroid is a member selected from the group consisting of testosterone, testosterone propionate, methyl testosterone, mesterolone, fluoxymesterone, methandriol, methandrostenolone, methenolone enanthate, nadrolone, morethandrolone, oxymetholone, stanozolol, zeranol, and mixtures thereof.

78. The method for administering a beneficially effective amount of the steroid to the animal over time according to claim 76 wherein the polymer is poly(2,2-dioxo-1,6-hexamethylene tetrahydrofuran) and the steroid is an androgenic steroid.

79. The method for administering a beneficially effective amount of the steroid to the animal over time according to claim 76 wherein the polymer is poly(2,2-dioxo-1,6-hexamethylene tetrahydrofuran) and the steroid is an estrogenic steroid.

80. The method for administering a beneficially effective amount of the steroid to the animal over time according to claim 76 wherein the polymer is poly(2,2-dioxo-1,6-hexamethylene tetrahydrofuran) and the steroid is a progestational steroid.

81. The method for administering a therapeutically effective amount of the steroid to the animal over time according to claim 76, wherein the cortical steroid is a member from the group consisting of aldosterone, desoxycorticosterone, cortisone, hydrocortisone, prednisone, prednisolone, triamcinolone, paramethasone, dexamethasone, fludrocortisone, flurandrenolone acetonide, betamethasone, benzoate, dexamethasone phosphate, methyl prednisolone, prednisolone acetate, and triamcinolone acetonide.

82. The method for administering a beneficially effective amount of the steroid to the animal over time according to claim 76 wherein the estrogenic steroid is a member selected from the group consisting of estradiol, 3-benzoate estradiol, 3-acetate estradiol, 17β-acetate estradiol, 17β-propionate estradiol, 17β-heptanoate estradiol, 17β-undecanoate estradiol, 17β-valerate estradiol, 3-methyl ether estradiol, 3,17β-diacetate estradiol, 3,17β-dipropionate estradiol, hemisuccinate estradiol, estradiol 17 β-cypionate, 17 β-estradiol disodium diphosphate, 17 β-estradiol disodium sulfate, 17 β-estradiol-3(disodium phosphate), 17 β-estradiol-17-(disodium phosphate), estriol, estrone, ethinyl, estradiol, estrazinol, estrofurate, guinestrol, and mixtures thereof.

83. The method for administering a beneficially effective amount of the steroid to the animal over time according to claim 76 wherein the progestational steroid is a member selected from the group consisting of progesterone, preganediol, algestone, acetophenide, azacosterol, chlormadinone acetate, dyhydrogesterone, ethisterone, hydroxyprogesterone, medrogestone, medroxyprogesterone, megestrol acetate, melengestrol acetate, allylestrenol, ethynodiol, diacetate, lynestrenol, norethindrone, norethindrone acetate, norethynodrel, norgesterone, norgestrel, norgestrienone, norvinisterone, oxogestone, quingestrone, quingestanol acetate, tigestol, and mixtures thereof.

84. The method for administering a beneficially effective amount of steroid to the animal according to claim 76 wherein the device is sized and shaped for placing topically on the skin and mucosa of the animal.

85. The method for adminstering a beneficially effective amount of the steroid to the animal according to claim 76 wherein the device is manufactured as a topical device comprising a backing member with the bioerodible polymer, the modified and the steroid on one surface thereof.

86. A device for delivering a beneficial drug at a controlled rate over a prolonged period of time, when the device is sized, shaped and adapted for delivering a drug to a drug receptor site, said device comprising (a) a polymer of the formula:

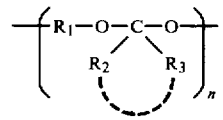

wherein $R_1$ is a member selected from the group consisting of alkylene of 1 to 10 carbons and alkenylene of 2 to 10 carbons; $R_2$ and $R_3$ are taken together forming a heterocyclic ring selected from the group consisting of dioxolanyl; dioxanyl; dioxepanyl; dioxocanyl; dioxonanyl; furyl, tetrahydrofruanyl; dihydrofuranyl; pyranyl; ocanyl; and oxepanyl; a nontoxic erosion rate modifier admixed with the polymer in an effective amount that cooperates with the polymer for regulating the rate of erosion of the polymer over time; a drug admixed with the polymer and the erosion rate modifier, which drug is released from the device to produce a beneficial therapeutic effect; and n is greater than 10.

87. The device for delivering a beneficial drug according to claim 86 wherein the drug is a member selected from the group consisting of local and systemic drugs, the polymer is poly(2,2-dioxo-1,6-hexamethylene tetrahydrofuran), and the erosion rate modifier is a member selected from the group consisting of a metal oxide, a salt of a nonmetal oxide, hydride, hydroxide, monobasic and polybasic acids, amines, and mixtures thereof.

88. The device for the delivery of a beneficial drug according to claim 86, wherein the drug is a member selected from the group consisting of cortical, androgenic, estrogenic and progestational steroids, and wherein the polymer is poly (2,2-dioxo-1,6-hexamethylene tetrahydrofuran).

89. The device for the controlled delivery of the beneficial drug according to claim 86 wherein the steroid is a member selected from the group of crotical hormones consisting of aldesterone, desoxycorticosterone, cortisone, hydrocortisone, prednisone, prednisolone, triamcinolone, paramethasone, dexamethasone, fludrocortisone acetate, flurandrenolone acetonide, betamethasone benzoate, dexamethasone phosphate, methyl prednisolone, prednisolone acetate, and triamcinolone acetonide, and wherein the polymer is poly(2,2-dioxo-1,6-hexamethylene tetrahydrofuran).

90. The device for the controlled delivery of the beneficial drug according to claim 86 wherein the steroid is an estrogenic hormone selected from the group consisting of estradiol, 17$\beta$-estradiol, 3-benzoate estradiol, 3-acetate estradiol; 17$\beta$-acetate estradiol, 17$\beta$-propionate estradiol, 17$\beta$-heptanoate estradiol, 17$\beta$-undecanoate estradiol, 17$\beta$-valerate estradiol, 3-methyl ether estradiol, 3,17$\beta$-diacetate estradiol, 3,17$\beta$-dipropionate estradiol, hemisuccinate estradiol, 17$\beta$-cypionate estradiol, 17$\beta$-estradiol disodium diphosphate, estriol, estrone, ethinyl estradiol, estrazinol, estrofurate, guinestrol, and wherein the polymer is poly(2,2-dioxo-1,6-hexamethylene tetrahydrofuran).

91. The device for the controlled delivery of the beneficial drug according to claim 86 wherein the device contains a dosage unit amount of a steroid selected from the group of progestational hormones consisting of progesterone, preganediol, algestone acetophenide, azacosterol, chlormadinone acetate, dyhydrogesterone, ethisterone, hydroxyprogesterone, medrogestone, medroxyprogesterone, megestrol acetate, melengestrol acetate, allylestrenol, ethynodiol diacetate, lynestrenol, norethindrone, norethindrone acetate, norethynodrel, norgesterone, norgestrel, norgestrienone, norvinesterone, oxogestone, quingestrone, quingestranol acetate, and tigestol, and the polymer is poly(2,2-dioxo-1,6-hexamethylene tetrahydrofuran).

92. The device for the controlled delivery of the beneficial drug according to claim 86 wherein the device administers a therapeutically effective amount of a steroid selected from the group of androgens consisting of testosterone, testosterone propionate, methyl testosterone, mesterolone, fluoxymesterone, methandriol, methandrostenolone, methenolone enanthate, nandrolone, norethandrolone, oxymetholone, stanozolol, and zeranol, and the polymer is poly(2,2-dioxo-1,6-hexamethylene tetrahydrofuran).

93. The device for the controlled delivery of the beneficial drug according to claim 86 wherein the device administers a therapeutically effective amount of a smooth muscle relaxant selected from the group consisting of amyl nitrate, glyceryl trinitrate, octyl nitrate, clonitrate, erythrityl tetranitrate, isosorbide dinitrate, mannitol hexanitrate and pentaerythritol, and the polymer is poly(2,2-dioxo-1,6-hexamethylene tetrahydrofuran).

94. A bioerodible ocular composition adapted for easy placement in an ocular environment, said composition comprising poly(2,2-dioxo-cyclohexane-dimethylene tetrahydrofuran), a dosage amount of a member selected from the group consisting of locally and systemically acting drugs administrable to the ocular environment, and a pharmaceutically acceptable bioerosion rate modifier in an effective amount that aids in controlling the rate of bioerosion of the composition in the ocular environment over time, whereby a therapeutically effective amount of drug is administered to the ocular environment over time.

95. The bioerodible ocular composition adapted for easy placement in an ocular environment according to claim 94, wherein the polymer has a cis/trans-1,4 cyclohexane isomeric configuration and the composition is manufactured as an ocular insert sized and shaped for easy placement and comfortable retention in the ocular environment.

96. The bioerodible ocular composition adapted for easy placement in the ocular environment according to claim 94, wherein the polymer comprises a cis/trans-1,4-cyclohexane isomeric structure, the composition is manufactured as an ocular insert, and the drug is a pharmaceutically acceptable antibiotic.

97. The bioerodible ocular composition adapted for easy placement in the ocular environment according to claim 94, wherein the polymer comprises a cis/trans-1,4-cyclohexane isomeric structure, the composition is manufactured as an ocular insert, and the drug is a pharmaceutically acceptable steroid.

98. A bioerodible ocular composition adapted for easy placement in an ocular environment of use, said composition comprising poly(2,2-dioxo-1,6 hexamethylene tetrahydrofuran), a dosage amount of a member selected from the group consisting of locally and systemically acting drugs administrable to the ocular environment in a therapeutically effective amount, and a pharmaceutically acceptable bioerosion rate modifier in an effective amount that aids in controlling the rate of bioerosion of the composition in the ocular environment over time, whereby a therapeutically effective amount of drug is administered to the ocular environment over time.

99. The bioerodible ocular composition adapted for easy placement in the ocular environment according to claim 98 wherein the drug is a pharmaceutically acceptable antibiotic.

100. The bioerodible ocular composition adapted for easy placement in the ocular environment according to claim 98 wherein the drug is a pharmaceutically acceptable steroid.

* * * * *